US011874965B2

(12) United States Patent
Rogers et al.

(10) Patent No.: US 11,874,965 B2
(45) Date of Patent: Jan. 16, 2024

(54) EPIDERMAL VIRTUAL REALITY DEVICES

(71) Applicants: NORTHWESTERN UNIVERSITY, Evanston, IL (US); THE BOARD OF TRUSTEES OF THE UNIVERSITY OF ILLINOIS, Urbana, IL (US)

(72) Inventors: John A. Rogers, Wilmette, IL (US); Shuai Xu, Chicago, IL (US); In Hwa Jung, Evanston, IL (US); Ha Uk Chung, Evanston, IL (US); Xinge Yu, Evanston, IL (US); Yu Yang, Evanston, IL (US); Jungyup Lee, Evanston, IL (US); Rujie Sun, Evanston, IL (US)

(73) Assignees: NORTHWESTERN UNIVERSITY, Evanston, IL (US); THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 203 days.

(21) Appl. No.: 17/466,094

(22) Filed: Sep. 3, 2021

(65) Prior Publication Data
US 2021/0397257 A1 Dec. 23, 2021

Related U.S. Application Data

(63) Continuation of application No. 16/481,209, filed as application No. PCT/US2018/015472 on Jan. 26, 2018, now Pat. No. 11,112,869.

(60) Provisional application No. 62/503,142, filed on May 8, 2017, provisional application No. 62/451,248, filed on Jan. 27, 2017.

(51) Int. Cl.
*G06F 3/01* (2006.01)
*H04W 4/80* (2018.01)
*G06F 1/16* (2006.01)
*G06T 19/00* (2011.01)

(52) U.S. Cl.
CPC .............. *G06F 3/015* (2013.01); *G06F 1/163* (2013.01); *G06F 3/016* (2013.01); *G06T 19/006* (2013.01); *H04W 4/80* (2018.02)

(58) Field of Classification Search
CPC .......... G06F 3/015; G06F 1/163; G06F 3/016; H04W 4/80; G06T 19/006
See application file for complete search history.

(56) References Cited

U.S. PATENT DOCUMENTS

| 5,165,897 A | * | 11/1992 | Johnson | ................. G06F 3/011 601/84 |
| 6,106,576 A | * | 8/2000 | Fromson | ................. A61H 1/00 318/16 |
| 9,741,216 B1 | * | 8/2017 | Keller | ..................... G06F 3/014 |
| 2003/0227374 A1 | * | 12/2003 | Ling | ..................... G09B 21/003 340/407.1 |

(Continued)

*Primary Examiner* — Nay Tun
(74) *Attorney, Agent, or Firm* — Locke Lord LLP; Tim Tingkang Xia, Esq.

(57) ABSTRACT

Provided are actuation devices, virtual reality devices formed from the actuation devices, and related virtual reality methods. The devices may comprise a plurality of spatially distributed actuators, each actuator configured for interacting with a biological skin surface; a wireless controller configured to receive operative command signals to control each of the actuators; and a wireless power system to power the actuators. Also provided are unique layouts of multiple interconnected devices to achieve large area coverage.

34 Claims, 27 Drawing Sheets

(56) References Cited

U.S. PATENT DOCUMENTS

| | | | | |
|---|---|---|---|---|
| 2005/0113167 A1* | 5/2005 | Buchner | .............. | A63F 13/285 463/30 |
| 2010/0141407 A1* | 6/2010 | Heubel | .............. | H04B 5/0037 340/407.1 |
| 2011/0102332 A1* | 5/2011 | Birnbaum | .............. | G06F 3/014 340/407.1 |
| 2011/0115709 A1* | 5/2011 | Cruz-Hernandez | ..... | G06F 3/016 340/407.2 |
| 2012/0067116 A1* | 3/2012 | Hilt | .............. | F04C 18/023 73/146.5 |
| 2012/0286935 A1* | 11/2012 | Huang | .............. | G01N 29/2481 340/10.1 |
| 2013/0041235 A1* | 2/2013 | Rogers | .............. | H05K 1/0283 600/386 |
| 2013/0333094 A1* | 12/2013 | Rogers | .............. | A61B 34/76 340/407.1 |
| 2014/0138432 A1* | 5/2014 | Park | .............. | G06K 19/0716 235/375 |
| 2016/0012689 A1* | 1/2016 | Evreinov | .............. | G08B 6/00 340/407.1 |
| 2016/0181868 A1* | 6/2016 | Casse | .............. | H01Q 1/248 307/104 |
| 2016/0262688 A1* | 9/2016 | Nichols | .............. | A61B 5/0024 |
| 2017/0095674 A1* | 4/2017 | Hresko | .............. | G09B 23/28 |
| 2017/0156662 A1* | 6/2017 | Goodall | .............. | A61N 2/002 |

* cited by examiner

Soft, conformal skin interface

| Mechanoreceptor | Best at Sensing (Modality) | Frequency Range |
|---|---|---|
| Merkel's Cells | Pressure (slower movements) | 0.4 - 100 Hz (5 - 15 Hz peak) |
| Ruffini Ending | Pressure (slower movements) | 7 Hz |
| Meissner's Corpuscle | Touch (faster movements), Vibration | 10 - 200 Hz (10 - 50 peak) |
| Pacinian Corpuscle | Vibration | 40 - 800 Hz (200 - 300 Hz peak) |

EPIDERMAL VIRTUAL REALITY DEVICES

CROSS-REFERENCE TO RELATED APPLICATIONS

This application is a continuation application of U.S. patent application Ser. No. 16/481,209, filed Jul. 26, 2019, which is a U.S. national stage application of PCT Patent Application No. PCT/US2018/015472, filed Jan. 26, 2018, which itself claims priority to and the benefit of U.S. Provisional Patent Application Nos. 62/503,142, filed May 8, 2017, and 62/451,248, filed Jan. 27, 2017, each of which is hereby incorporated by reference in its entirety.

BACKGROUND OF INVENTION

Provided herein are arrays of wireless sensors and actuators for virtual reality applications. The devices and related methods are useful for a wide range of applications, including wearable electronics, virtual reality, personal monitoring and medical devices.

With the continued development of electronic communications and social media, platforms for social interactions continue to gain popularity. With video communication, including over those social platforms as well as in the gaming and training fields, what continues to lag is the ability to reliably and comprehensively physically interact at a distance in a manner that is both unobtrusive and realistic with the corresponding video interaction. Although much effort has been devoted to producing devices to immerse a user in a virtual reality, those devices suffer from significant disadvantages, including the ability to reliably power and communicate with those devices in a light-weight, wireless and unrestricted manner.

For example, U.S. Pat. Pub. 2015/0022328 suffers from power limitations, requiring a power supply or physical connection to another device, such as a "mobile device" or power supply. PCT Pub. NO. 2014204323 describes sensors integrated into fabrication of a wearable item, but is of limited value as actuators are not included. U.S. Pat. Pub. 2014/0070957 and U.S. Pat. No. 7,967,679 may be characterized as describing provision of forces, but the devices described therein are bulky, complex, and require significant and bulky hardware that is simply not conducive for a comfortable and reliable virtual reality experience.

With the ongoing development of miniaturized electronic systems (see, e.g., WO 2016/196675; WO 2013/149181; U.S. 2013/0041235; U.S. Provisional App. No. 62/451,248 titled Body-Mounted Wireless Sensors and Actuators filed Jan. 27, 2017 (Rogers et al.)), each of which are hereby specifically incorporated by reference, a platform is available to simplify the virtual reality device in a manner that is light-weight, form-fitting and compatible with conventional manufacturing platforms. Challenges remain, however, with reliably powering and communicating with the devices, particularly for devices having multiple actuators for affecting a detectable physical experience to a user. Such actuators, particularly for a force generation, are notoriously power demanding. The devices and methods provided herein address this problem by incorporating unique power-saving platforms so that the devices remain wireless and are not limited to being hooked into relatively bulky power sources, even up to very large area coverage systems with a large total number of actuators.

SUMMARY OF THE INVENTION

The devices, including actuation devices and virtual reality devices, are specially configured to provide the ability to reliably generate and impart an action, even relatively energy-intensive forces, that can be felt by a user, and that is compatible with a wireless configuration. This is achieved through the use of wireless power, communication and control systems. A special challenge is in providing sufficient power to actuate mechanical and/or thermal actuators that are distributed over a surface of user. In certain examples herein, this is achieved by providing one controller that controls a plurality of actuators, and rapidly switching the controllers on and off in a manner such that only one single actuator is powered at a time. The switching, however, may be at a sufficiently high rate that the user experiences a feeling of all the actuators being simultaneously energized. In this manner, the total power requirements at any given time may be reduced so that sufficient power is maintained, even for relatively prolonged actuations over large surface areas of the body. Of course, the systems provided herein are similarly compatible with actuators that are sufficiently separated so that a user can recognize different regions of the skin that are receiving an actuation by the actuator.

Also provided are unique configurations of actuators that allow a controller to rapidly and reliably exert any of a variety of forces on a user at a distance. Two-way communication with the controller, including optionally with sensors independently monitoring the user, allows for the controller to confirm that the user is experiencing the desired forces and to assess any biological responses thereto. The systems are compatible with use of a pair of virtually reality devices, essentially allowing the user to be a controller, and vice versa as well. The systems may also be in two-way communication with each other, such that one actuation device or system is in two-way communication with other actuation devices or systems.

Provided herein are various actuation devices for a range of applications, including for simulation of a remote or artificial environment or encounter, such as for virtual reality applications. For example, an actuation device may comprise a plurality of spatially distributed actuators. Each actuator is configured to interact with a biological skin surface. A wireless controller is operably connected to the actuators and configured to receive operative command signals to control each of the actuators. In this manner, an individual at a distance may control, as desired, actuation of the actuators of the device that is being used by a second individual, without any direct physical contacts or physical connections between the individuals. A wireless power system is operably connected to power the actuators. The wireless power system is selected to provide sufficient power to reliably power and control the actuators. For example, any of the actuator devices provided herein may be defined by a wireless power system that provides defined power harvesting level, such as a power harvesting that is greater than or equal to 5 mW, including greater than or equal of 5 mW and less than or equal 5 W, or between about 10 mW and 500 mW, or between about 5 mW and 500 mW, and any subranges thereof. The devices provided herein may be compatible with a range of wireless power systems, so long as sufficient power is harvested for powering the actuators and controlling and communicating with the device, while still being able to reliably and relatively unobtrusively interact or interface with the skin. Certain applications and associated actuators may require more power than others. For example, actuators that are electrodes to generate a short burst electric field may require less power than a mechanical actuator that functions by a high frequency movement of a component against the skin, or a thermal actuator (e.g., a heater) to heat the skin.

Other parameters may be used to describe the wireless energy harvester. For example, any of the actuation devices may be described as providing a minimum level of power harvesting, including as described above (e.g., 5 mW); a power delivery of at least $5 \times 10^{-4}$ mW/cm$^2$ and less than $5 \times 10^{-2}$ mW/cm$^2$; and/or a power efficiency defined as power delivered to power harvested that is greater than or equal to 50%. The relatively modest power requirements reflect various low power configurations, including as explained below by rapid power-switching circuits associated with the actuators.

Any of the actuation or virtual reality devices may further comprise a sensor operably connected to the wireless controller and the wireless power system for sensing a physical parameter. Such sensing capability provides additional level of control and two-way interaction, with a remote controller being able to independently, quantitatively, and reliably assess how the actuators are functioning and how the user is responding to the actuation stimulus or stimuli. The sensor may also be used in a feedback-control loop configuration, to ensure the actuators are providing the desired level of actuation stimuli.

The devices provided herein may be further described in terms of the wireless power system. For example, any of the devices may have a large area antenna for wireless power harvesting and powering of the actuators. The large area antenna may have a length that is greater than or equal to 100 cm. The large area antenna may have a length, thickness, and material property selected to provide the desired power harvesting, including for the application of interest. Large lengths of the large antenna are achieved by coiling around a relatively large area of a substrate on which the device is supported or which forms a base of the device. The antenna may be embedded in a polymer substrate, including confined at an edge region, such as the outer-most 10% or 5% of the total supporting surface substrate surface area.

Any of the devices and methods provided herein may use wireless power systems together with local power storage, including in the form of batteries or supercapacitors.

Similarly, any of the devices provided herein may further comprise a small area antennae for powering a wireless controller, such as less than or equal to a perimeter footprint of 10 cm. Longer lengths are achieved by coiling. In this manner, an actuator device or virtual reality device may have a pair of antennas, with the large area antenna harvesting more power to satisfy the relatively high power demands of the actuators. The small area antenna, in contrast, may harvest relatively less power and be used for powering and communication with the wireless controller.

The wireless controller may comprise a NFC chip that can communicate with a nearby electronic device in a wireless fashion, including one- or two-way communication. That nearby electronic device may then communicate data, in either direction, including to and from a remote user having a graphical user interface (GUI) displaying status of the actuator devices, with a more capable form of wireless communication.

The plurality of spatially distributed actuators may be distributed over a surface area at a density matched to the desired application of interest. For example, in areas of the body having a higher sensitivity to physical stimulus, a higher density of actuators may be deployed. In contrast, areas of the body having lower sensitivity or importance may have a relatively lower density. The devices may be deployed in a tiled configuration, in that "patches" of actuator devices are distributed over the body, with each patch containing a plurality of actuators. In such a manner, while each device may have a relatively small footprint, such as ranging from between 1 cm$^2$ and 500 cm$^2$, large total surface area distribution and coverage can be achieved. For example, an actuator distribution surface area that is greater than or equal to 1 m$^2$.

The actuators, and related components, may be provided on a substrate, such as a flexible substrate. In this manner, the actuators may be described as having a density on the substrate, defined by the number of actuators divided by the area of the surface supporting the actuators. For example, seven actuators are readily positioned on a 3"×3" substrate, corresponding to an actuator density of 0.12 actuators/cm$^2$, or about 1 actuator per 8.3 cm$^2$. Provided herein are actuator densities ranging from sparsely distributed to densely distributed, such as between 0.01 actuator/cm$^2$ to 1 actuator/cm$^2$.

As described, the device may comprise a plurality of individually interconnected flexible substrates, wherein each of the individual substrates support a plurality of actuators and are individually positionable over a desired skin area during use. In this manner, "clusters" of actuators are provided in desired locations, without necessarily having to sacrifice a desired substantially whole body or even whole body coverage. For example, in a game where physical forces are to be experienced, such as blunt or acute force, the front, back and side torsos, head, each leg and each arm may have a region of dense coverage to realistically reflect a force to those regions. In contrast, for a sporting game such as golf, baseball, tennis or soccer, more coverage may be devoted to the hands or feet to reflect a realistic impact with the ball. The devices provided herein are accordingly compatible and tailored to any of a variety of applications and interactions by covering the body in a desired layout so as to best reflect the expected virtual reality transmitted interactions.

The device itself is readily scalable, and may have two or more actuators, such as a flexible substrate that supports from between 4 to 500 actuators. The device may be configured for a reversible interface with skin. In this manner, after use, the device is removed without damaging the components and can used again at a later time, including with a different individual. Accordingly, the devices may be cleaned or disinfected without any adverse impact on functionality. As desired, to better protect the device components, any of the devices may be encapsulated with an encapsulation layer to increase device longevity without sacrificing functionality. This is achieved by using relatively soft, flexible and bendable material in the encapsulating layer, such as a polymer.

The flexible substrate may comprise a fabric, including a fabric that is part of clothing. Particularly useful are stretchable and form-fitting fabrics, including synthetic fabrics that elastically fit to the body, including shirts, pants, shorts, undergarments, hats, face coverings, socks, foot covering, hand or finger covering, and the like.

The devices are compatible with a range of actuators, including a mechanical actuator, a thermal actuator, an electrical actuator, and combinations thereof. Other actuators are selected based on the application of interest. For example, chemical or biological actuators may release an active agent that interacts with biological components on or underneath the skin. For charged agents, or agents connected to a charged carrier, the application may be under an applied electric field, wherein the electric field is not felt by a user.

The mechanical actuator may be described as having a vibration frequency that is greater than or equal to 1 Hz and less than or equal to 1 kHz, including frequencies matched to biological mechano-transducers, including mechanoreceptors, underlying the device, including between 100 Hz and 300 Hz, 150 Hz and 250 Hz, and any subranges thereof.

The mechanical actuator may comprise an electrically conductive coil and a magnet, wherein the magnet is positioned within a magnetic field generated by the electrically conductive coil when an electric potential is applied to the electrically conductive coil. In this manner, switching the applied electric signal to the coil on and off imparts a corresponding vibration frequency to the magnet, and the oscillating magnet is sensed as a pressure-type impinging force by the body during use.

The electrically conductive coil and the magnet may be separated by a gap, such as a gap between about 0.1 mm and 0.5 mm. A thin cover layer, such as between about 5 and 50 µm, or between about 10 µm and 20 µm, including of PI, is positioned above the magnet to provide the desired gap.

The mechanical actuator may further comprise a polymer layer having a recess, wherein the magnet is positioned in the recess and the electrically conductive coil is positioned below the magnet.

A switch may be provided that is electronically controlled by the wireless controller for oscillating electrical energization of the electrically conductive coil between off and on states, thereby generating a controlled vibration frequency of the magnet. The magnet vibration frequency may be between 100 Hz and 300 Hz.

The actuator may be a thermal actuator, including one having a resistive wire that heats under an applied electric current. For example, a gold wire having a width of between 10 µm and 200 µm with a thermal heating area that is between 1 mm$^2$ and 50 mm$^2$. In this manner, the actuation device may comprise both a thermal actuator and a mechanical actuator. More intense, higher frequency actuation over longer durations can then also be signaled to the user by heating with the thermal actuators. Any combination of actuators may then be used to further increase the reality of the transmitted actions. For example, a pressure exerted by an actuator to reflect a droplet of water running down a surface may also result in release of moisture or water from an actuator that releases moisture or water. To avoid unwanted moisture build-up, the substrate may be formed of a moisture-breathable, wicking or removing material.

The devices, including actuation and virtual reality devices, described herein may comprise a low power electric circuit. The low power electric circuit may comprise a single wireless controller that controls the plurality of spatially distributed actuators and that electrically energizes a single actuator at a time with the other actuators in an off-state.

The wireless controller may be an NFC chip having a plurality of outputs, with each output electronically connected to an individual actuator, the device further comprising a switch electronically positioned between the NFC chip output and the actuator to provide the individual actuator electrical energization at a switching frequency. The switching frequency between actuators may be faster than a mechanoreceptor reaction time for a mechanoreceptor that is positioned beneath the actuation device during use, so that a simultaneous actuation of all the plurality of actuators is experienced by a user to whom the actuation device interfaces, even though only a single actuator at a time is actuated. In this manner, the effective footprint of the actuator is expanded beyond the footprint of a single actuator, including corresponding to at least 80%, at least 90%, or approximately the entire footprint of the substrate supporting the actuators.

Any of the devices described herein may further comprise a sensor in electronic communication with the wireless controller for measuring a physical parameter. In this manner, two-way communication may occur, with the sensor feeding a signal to a remote controller or user to display information about the state of the person experiencing the actuation.

Also provided herein are virtual reality devices or actuation systems comprising a plurality of any of the actuation devices described herein. For example, each of the actuation devices may be in wireless communication with each other. The wireless communication may comprise bidirectional communication, including between devices and/or between the devices and remote controller/displayer.

Each of the actuation devices may further comprise a sensor for sensing a physical parameter, wherein the sensor is in electronic communication with the wireless controller so that a sensor output may be communicated to a different actuation device or an external controller.

Any of the actuation devices or systems may be part of a virtual reality device.

Also provided herein are virtual reality devices comprising a plurality of spatially distributed biologically interactive devices configured for interacting with a biological surface, such as the outer-facing skin surface. The biologically interactive devices may each comprise a sensor and an actuator. A wireless controller configured to receive operative command signals may control each of the biologically interactive devices and transmit to a remote controller output from each of the sensors. A wireless power source may be operably connected to the plurality of biologically interactive devices.

The plurality of spatially distributed biologically interactive devices may be configured to generate a coordinated and spatiotemporally varying output of heat, electrical stimulation, mechanical vibration, or any combination thereof. They may also receive a specified input from a controller (e.g., a person remotely interacting with the user) and provide a corresponding actuation to the user.

The virtual reality device may be configured for person-to-person interaction, further comprising a computer interface for control at a distance by a person of the plurality of spatially distributed biologically interactive devices. By pairing the devices, there may be two-way interaction.

The virtual reality device may be used with any application where it is desired for one or more parameters to be effected on an individual, such as for gaming, training, communication, or pleasure.

The sensors may be configured to modulate the actuators based on a one or more physiological parameter measured by the sensors. The physiological parameters include, but are not limited to, temperature; pressure; motion; location; or strain.

The wireless controller may comprise a near field communication (NFC) chip to provide wireless power delivery to the sensors and actuators and wireless data communication between the biologically interactive devices and an external controller.

The wireless controller may provide two-way communication with the plurality of biologically interactive devices to acquire physiological parameter data from the plurality of sensors and to operate the actuators of the plurality of biologically interactive devices. The wireless controller may comprise a long-range reader so that some freedom of movement is afforded to an individual connected to the actuators of the device without losing signal being sent to a remote operator.

The virtual reality device may be configured to provide sensing and actuating capabilities of an effective body surface area corresponding to at least 70% of a living animal skin surface.

The virtual reality device may have a maximum wireless transmission and receipt range that is greater than or equal to 10 cm, and optionally with an upper cut-off that is less than or equal to 1 m.

The plurality of biologically interactive devices may be directly or indirectly skin-mounted and provides a spatial distribution map of the physiological parameter, such as to a display in real-time and/or is recorded for later use. Directly mounted refers to direct placement on the skin, and may include the use of adhesives, similar to an adhesive bandage that can be removed, as desired. Alternatively, the device may be mounted in clothing or the like, with the clothing or the like worn by the user with a type of "automatic" interfacing with the actuators. This can be particularly useful instead of individually mounting devices all over the body separately.

Accordingly, the plurality of biologically interactive devices may be configured to directly connect to a skin surface of a living animal. Alternatively, the plurality of biologically interactive devices may be embedded or connected to a garment, wherein the garment is configured to be worn by a living animal to provide the plurality of biologically interactive devices adjacent to a skin surface.

The virtual reality device may comprise at least 20 biologically interactive devices. Each biologically interactive device may itself comprise a single actuator or a plurality of actuators, such as 2-20, 4-10, or any subrange thereof.

Each biologically interactive device may comprise a NFC chip for wireless communication and control and a wireless energy harvester comprising a large area antenna for powering the actuators.

The sensor may comprise a temperature sensor and a pressure sensor. The pressure sensor may comprise a silicon pressure sensor formed from an ultrathin spiral shape layer of monocrystalline silicon. The pressure sensor may comprise a layer of silicon positioned between a top polymer layer and a bottom polymer layer.

The virtual reality device may further comprise a magnetic inductive loop antenna configured to wirelessly interface with an external reader antenna. The external reader antenna may be embedded in an external reader antenna substrate, including the substrate that also supports the actuators.

The virtual reality device may further comprise a remote controller that provides wireless commands to the wireless controller for remotely controlling the plurality of actuators.

Each biologically interactive device may be multifunctional and measure and/or control at least temperature and pressure.

Each biologically interactive device may measure at least one additional parameter selected from the group consisting of: oxygen level, electric potential, heart rate, respiration rate, hypovolemia, and optical signal. Any of the devices and methods may be used to measure a physiological parameter that is pressure, temperature, galvanic skin response, impedance, thermal transport, sweat release, blood flow, blood oxygenation, thermal properties, electrical impedance, modulus, sweat, biopotential (emg, eog, eeg, and the like), shear stresses, normal stresses (pressure), and the like, and any combination thereof. For example, any of the devices and methods may have a pressure sensor and/or a temperature sensor to measure pressure and/or temperature. Optionally, one or more additional physiological parameters may be measure in addition to pressure and temperature. Any of the devices and methods may be for measuring a physiological parameter of skin. Any of those measurements may then be used by any of the actuators described herein to effectuate a biological response, such that there is a built in feedback loop, with sensors used to determine appropriate actuation states, magnitude and/or spatial distribution of actuation.

Also provided herein are actuation systems or virtual reality devices, comprising a plurality of any of the devices described herein. For example, each of the plurality of devices may be an actuation device comprising a plurality of spatially distributed actuators, each actuator configured for interacting with a biological skin surface; a wireless controller configured to receive operative command signals to control each of the actuators; a wireless power system to power said actuators; and a flexible substrate that supports each of the actuators, wireless controller and wireless power system. Each actuation device may be in wireless communication with at least one other of the actuation devices.

The devices and methods provided herein may incorporate a full range of actuator modalities, including static or dynamic forces, static or dynamic temperature, electrical stimulation, including in combination with inputs from any of the sensors described herein. This combination of sensor and actuator configurations may be independently controlled, may be in a closed feedback loop configuration, and may have any of a range of spatial configurations depending on the application of interest.

The wireless communication between actuation devices may be in a two-way communication, so that the actuation device sending a signal out may also receive a signal back. For example, each of the actuation devices may further comprise a sensor, including so that an output from at least one sensor is communicated to another actuation device to control another actuation from another device actuator.

Also provided herein is a method of virtual interaction with an individual using any of the actuation or virtual reality devices formed therefrom. For example, the method may comprise the steps of: providing a plurality of actuators spatially distributed over a skin surface of an individual; wirelessly connecting the actuators to a remote controller; inputting to the remote controller an input signal to activate at least a portion of said actuators and interface with the skin surface; and wirelessly powering the activated actuators in a low power mode, wherein the low power mode comprises rapid switching between activated actuators so that the individual experiences a physical sensation of all actuators activated simultaneously, even though only one actuator at a time is actively powered.

A method of virtual interaction with an individual may comprise the steps of providing any of the actuator devices, systems or virtual reality devices described herein adjacent to a skin surface of an individual; wirelessly connecting the actuators to a remote controller; inputting to the remote controller an input signal to activate at least a portion of the actuators and to remotely interface with the skin surface; thereby virtually interacting with an individual.

The method may further comprise sensing one or more physical parameters with a sensor; and transmitting an output from the sensor to the remote controller, thereby providing feedback to a remote user of the remote controller.

Each biologically interactive device, including an actuator, may have a footprint that is less than or equal to 5 cm$^2$; and a thickness that is less than or equal to 1 cm. The underlying actuators may provide high fidelity, such as high sensitivity and precision. For example, the device may have: a temperature precision of at least 0.1° C., a thermal mass density that is less than that of skin and less than 75 µJ/mm$^2$/K, and/or a thermal equilibrium response time that is less than or equal to 3 seconds.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
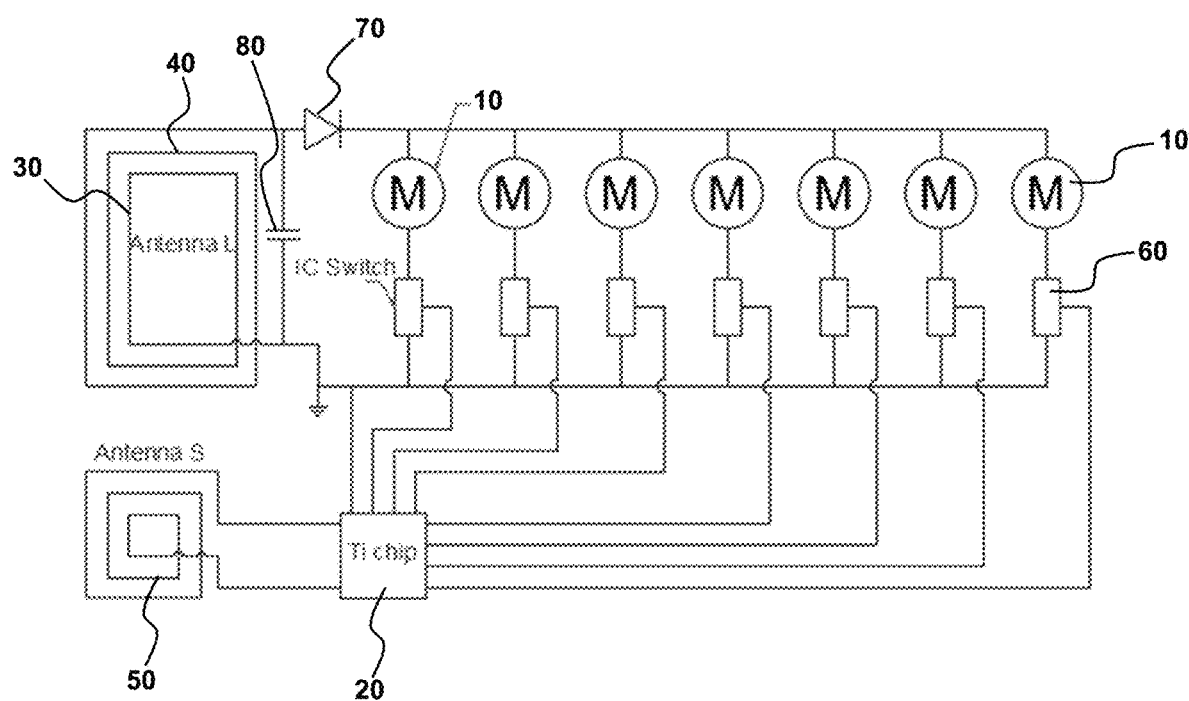
FIG. 1. Circuit schematic of a seven-actuator device powered by a large antenna and controlled by a chip powered by a small antenna. Switches may be incorporated into the circuit to provide rapid on/off of individual actuators, including by use of IC switches. Rapid switching provides the ability to power multiple actuators in a manner such that an individual has a physical sensation that all actuators operate simultaneously, although only a single actuator at a time is powered. In this manner, power usage is minimized and is compatible with the power generated by the large antenna, particularly for power-intensive actuators.

In general, the terms and phrases used herein have their art-recognized meaning, which can be found by reference to standard texts, journal references and contexts known to those skilled in the art. The following definitions are provided to clarify their specific use in the context of the invention.

"Wireless controller" refers to an on-board chip and other electronic components that provides the ability to remotely control the actuators and other controllable components, such as sensors, as well as data communication requirements, without a physical connection. In certain embodiments, a controller may also refer to the electronics/computing and ancillary components that a remote individual uses in order to control an actuator device that is worn or otherwise mounted to another individual, generally referred herein as an "external controller".

"Power harvesting" refers to a process by which energy is derived from an external source and, thereby, may avoid the need for relatively large, bulky and expensive primary or secondary battery systems. Of course, the devices provided herein may be compatible with batteries and/or supercapaciters, depending on the application of interest. For example, relatively heavy or bulky systems may be incorporated into clothing, shoes, hats, gloves, scarves, face masks, and the like, in a manner that would be unobtrusive, or minimally noticeable, to a user.

Outer perimeter refers to the length of a single coil of the antenna, and reflects the footprint occupied by the antenna. For a small area antenna, it may be 10 cm. For a large area antenna, it may be as high as the outer perimeter of the device, such as 40 cm. By increasing the number of coils, a range of lengths may be attained.

"Effective body surface area" refers to the effective coverage of the virtual reality devices provide herein. By specially grouping actuators and sensors together, and then using a plurality of those groups, large surface area coverage is possible. Such large surface area coverage may be facilitated by placing the devices in clothes and coverings that are worn on the body. Use of such groupings increases the effective surface area of actuation.

"Flexibility" or "bendability" refers to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and open or mesh geometries.

"Spatially distributed" refers to an arrangement of actuators or sensors such that they are independently controllable and interface with different locations of the skin surface. Depending on the context, spatially distributed may refer to the position of a device on the skin, or may refer to the positions of each of the plurality of actuators relative to each other.

"Interact" refers to the ability of an actuator to effect a change in the underlying surface. The change may be via a receptor-mediated change, such as a physical force, temperature, pressure, that is detected by an individual via mechanotransduction and subsequent nerve impulse, or by a chemical-mediated receptor binding and signal transduction. "Interface" refers to the ability of an actuator to interact with the surface, or a sensor to detect a physical parameter of the surface.

"Operably connected" refers to a configuration of elements, wherein an action or reaction of one element affects another element, but in a manner that preserves each element's functionality. For example, a wireless controller such as an NFC chip operably connected to an actuator refers to the ability to energize the actuator in accordance with a control command received by the controller without impacting the functionality of the wireless controller and actuator.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. As used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island—bridge geometry. Stretchable device components include structures having stretchable interconnects, such as stretchable electrical interconnects. As used herein, for embodiments where the devices are mounted directly to the skin, the devices may be characterized as stretchable, including stretchable and flexible so as to achieve good conformal contact with underlying skin, if desired. "Conformable" refers to a device, material or substrate which has a bending stiffness sufficiently low and elasticity sufficiently high to allow the device, material or substrate to adopt a desired contour profile, including a contour profile that may change over time, for example a contour profile allowing for conformal contact with a surface having a pattern of relief or recessed features, or. In certain embodiments, a desired contour profile is that of a tissue in a biological environment, for example skin or the epidermal layer.

"Adjacent" to the biological surface or to the skin refers to positioning the device so that the actuator may interface with the underlying biological material. The interface may be by a physical force, such as a pressure exerted on the surface, an electrical stimulus, an optical signal, or heating, or may be a more biological or chemical interface, such as release of a biological or chemical agent. Similarly, adjacent in the context of sensors interfacing with the surface, refers to the ability of the sensor to measure a parameter of interest on the skin or beneath the skin, such as blood flow, oxygen level, temperature, optical parameter, tissue stiffness, moisture level, or the like. Accordingly, a device may be considered adjacent if it is directly mounted to the surface, or has an intervening layer, including an adhesive and/or barrier layer, so long as the functionality of the actuator or sensor is maintained. Adjacent may also be described as within 1 mm, 500 µm, 100 µm, 10 µm or 1 µm of the skin surface.

"Wireless controller" refers to electronic components, including chips, that provide for wireless control of the actuators. An example of a wireless controller is a near field communication (NFC) chip, including NFC chips from Texas Instruments. NFC is a radio technology enabling bi-directional short range wireless communication between devices. In this manner, a controller external to the actuator device (e.g., off-circuit) can be used to provide actuator control and to receive information from the actuator device, including device status or information from one or more on-circuit sensors.

"Substrate" refers to a material having a surface that is capable of supporting a structure, including any electronic device or electronic device component described herein, including actuators, sensors, antennae, and related circuitry. Supporting includes components at least partially or fully embedded in the substrate. A structure that is "bonded" to the substrate refers to a portion of the structure in physical contact with the substrate and unable to substantially move relative to the substrate surface to which it is bonded. Unbonded portions, in contrast, are capable of substantial movement relative to the substrate.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, graft, tapered and other copolymers. Useful polymers include organic polymers or inorganic polymers and may be in amorphous, semi-amorphous, crystalline or partially crystalline states. Cross linked polymers having linked monomer chains are particularly useful for some applications. Polymers useable in the methods, devices and device components include, but are not limited to, plastics, elastomers, thermoplastic elastomers, elastoplastics, thermostats, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulfone based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and return to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers useful include, but are not limited to, thermoplastic elastomers, styrenic materials, olefenic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefenic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a flexible polymer is a flexible elastomer.

"Young's modulus" and "modulus" are used interchangeably and refer to a mechanical property of a material, device or layer which refers to the ratio of stress to strain for a given substance. Young's modulus may be provided by the expression;

$$E = \frac{(\text{stress})}{(\text{strain})} = \left(\frac{L_0}{\Delta L}\right)\left(\frac{F}{A}\right),$$

where E is Young's modulus, $L_0$ is the equilibrium length, $\Delta L$ is the length change under the applied stress, F is the force applied and A is the area over which the force is applied. Young's modulus may also be expressed in terms of Lame constants via the equation:

$$E = \frac{\mu(3\lambda + 2\mu)}{\lambda + \mu},$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably 10 times larger for some applications, more preferably 100 times larger for other applications and even more preferably 1000 times larger for yet other applications. "Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire layer of material.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

"Encapsulate" refers to the orientation of one structure such that it is at least partially, and in some cases completely, surrounded by one or more other structures. "Partially encapsulated" refers to the orientation of one structure such that it is partially surrounded by one or more other structures. "Completely encapsulated" refers to the orientation of one structure such that it is completely surrounded by one or more other structures. The invention includes devices having partially or completely encapsulated electronic devices, device components and/or inorganic semiconductor components.

A "component" is used to broadly refer to an individual component within an electrical, optical, mechanical or thermal device. Components include, but are not limited to, a photodiode, LED, TFT, electrode, semiconductor, other light-collecting/detecting components, transistor, integrated circuit, contact pad capable of receiving a device component, thin film devices, circuit elements, control elements, microprocessors, transducers and combinations thereof. Electrical device generally refers to a device incorporating a plurality of device components, and includes large area electronics, printed wire boards, integrated circuits, device components arrays, biological and/or chemical sensors, physical actuators and sensors (e.g., temperature, light, radiation, etc.).

"Sensor" refers to a device component useful as a sensor and/or useful for detecting the presence, absence, amount, magnitude or intensity of a physical property, object, radiation and/or chemical. Sensors in some embodiments function to transduce a biological signal into an electrical signal, optical signal, wireless signal, acoustic signal, etc. Useful sensing elements include, but are not limited to electrode elements, chemical or biological sensor elements, pH sensors, optical sensors, photodiodes, temperature sensors, capacitive sensors strain sensors, acceleration sensors, movement sensors, displacement sensors, pressure sensors, acoustic sensors or combinations of these.

"Actuator" refers to a device component useful for interacting with, stimulating, controlling, or otherwise affecting an external structure, material or fluid, for example a biological tissue. Useful actuating elements of the actuator include, but are not limited to, electrode elements, electromagnetic radiation emitting elements, light emitting diodes, lasers, magnets in an oscillating magnetic field, chemical or biological release agents, and heating elements. Actuators include electrodes for providing a voltage or current to a tissue, heaters for providing heat to a tissue, mechanical actuators for generating force or pressure to a tissue. Actuators may include sources of electromagnetic radiation for providing electromagnetic radiation to a tissue. Actuators include thermal sources for heating tissue. Actuators include displacement sources for displacing or otherwise moving a tissue.

Example 1: Actuator-Containing Devices

FIGS. 1-2, 3A and 3B describe a demonstrator actuator device, having a 3"×3" square footprint with seven independently-controlled actuators spatially separated, in this example in a circular array configuration with one actuator at the origin and the other spatially distributed around the central actuator at the origin. The device is wireless and can be operated without batteries, if desired. Furthermore, the device is readily scaled to have any size footprint, and may be tiled across the body, without limitation. The device has a range of design flexibility, including in size, shape and form factor, and has mechanical characteristics described as soft, flexible and bendable. The devices are readily manufactured.

Figure 2:
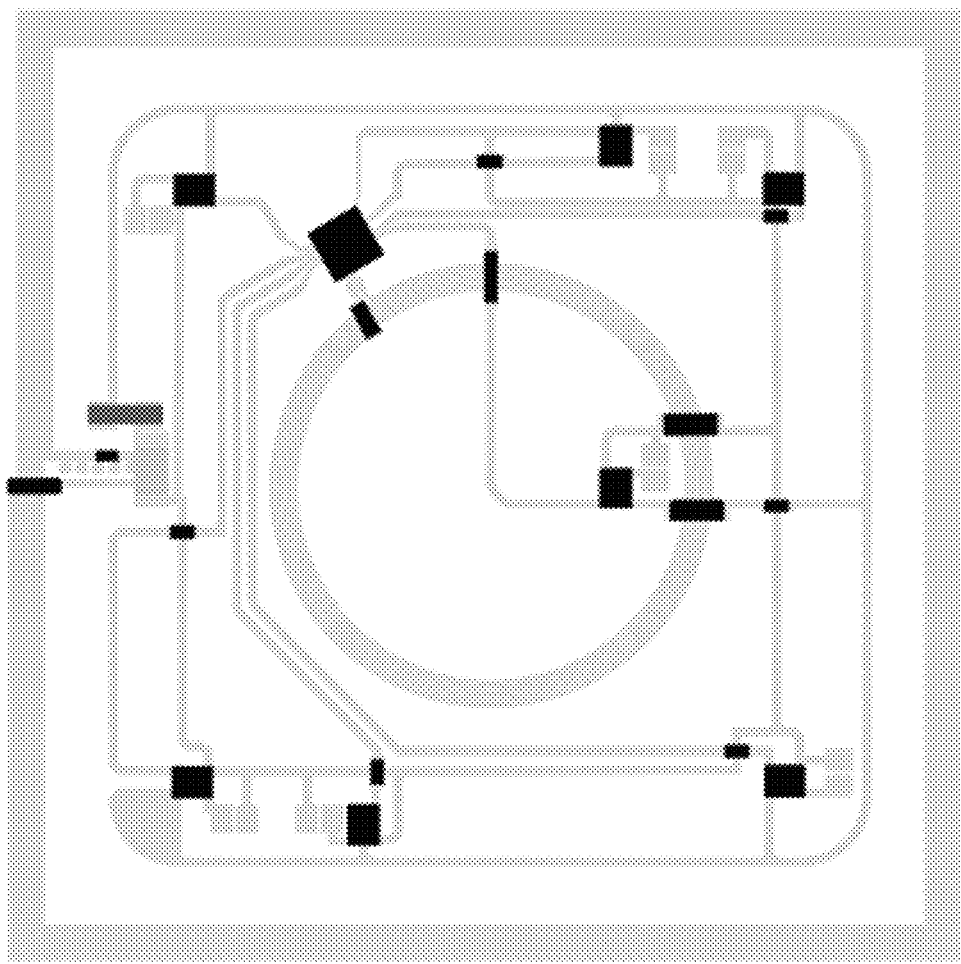
FIG. 2. Circuit layout for the seven-actuator device of FIG. 1.
Figure 3A:
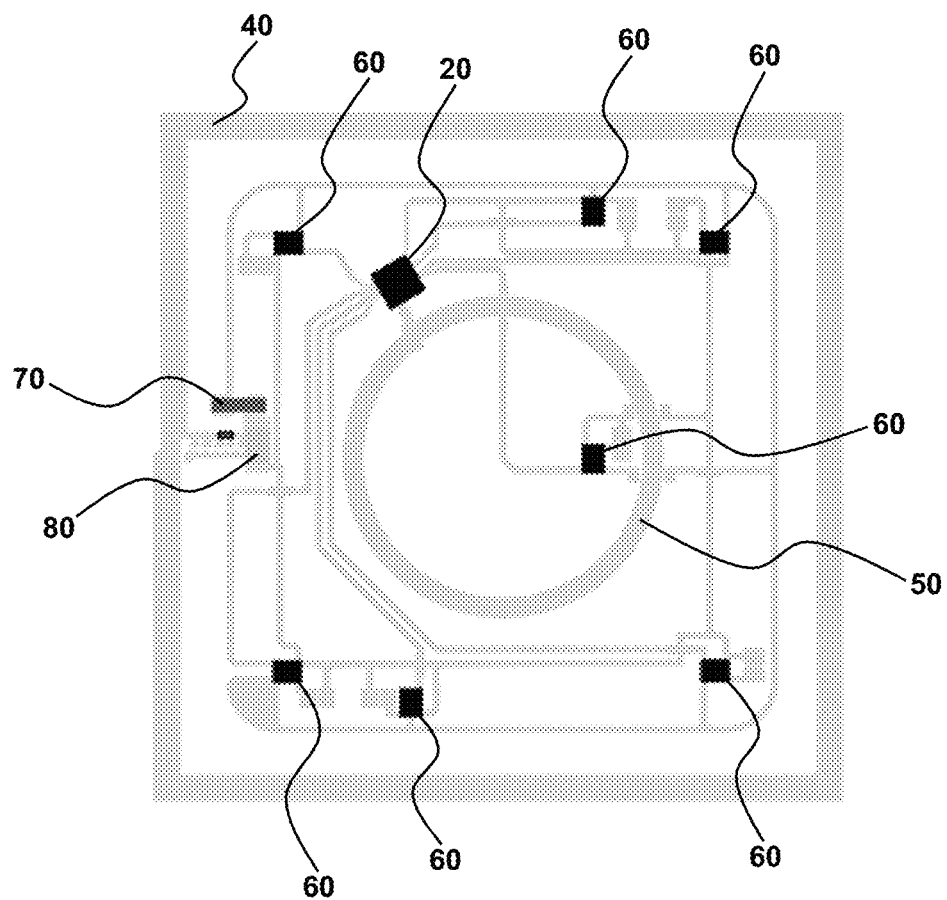
FIG. 3A labels various components of the circuit of FIG. 2 and FIG. 3B includes the actuators in the circuit.
Figure 3B:
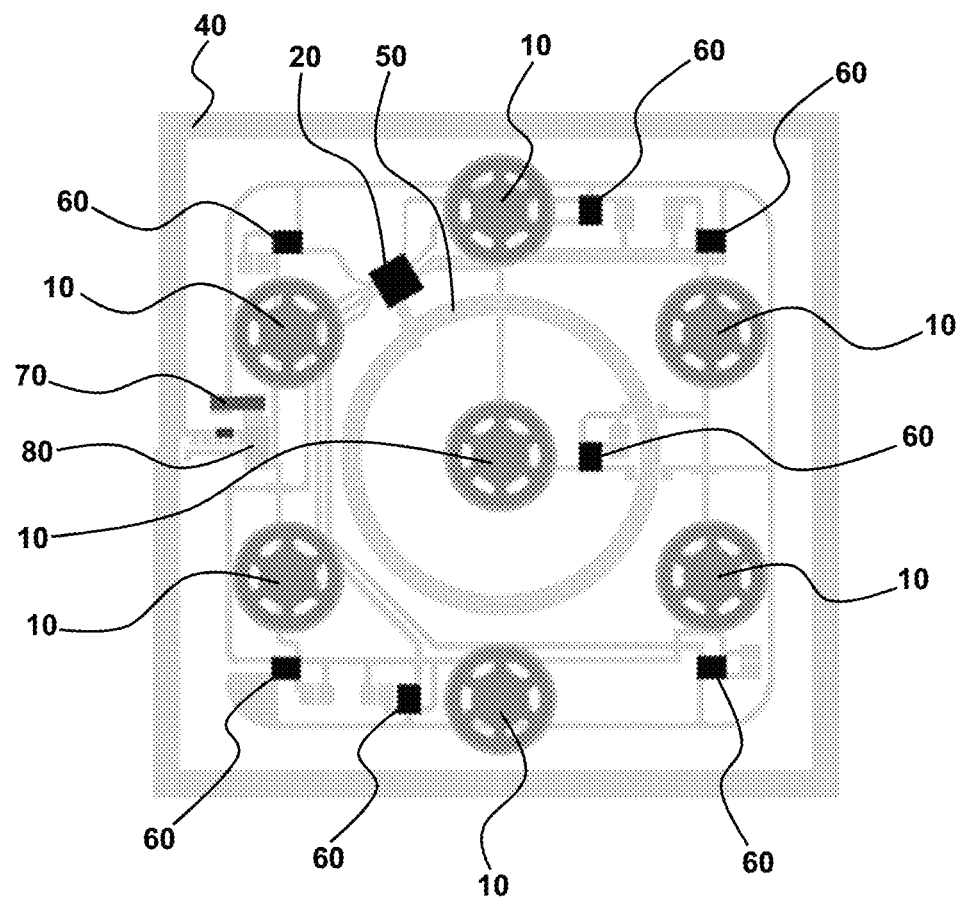

FIG. 1 is an actuation device circuit schematic showing a plurality of spatially distributed actuators 10 connected to a wireless controller 20 and a wireless power system 30. The wireless power system may comprise a large area antenna 40 for wireless power harvesting and powering of the actuators. A small area antenna 50 may power and send operative command signals (e.g., communication signal) to the wireless controller 20. A single wireless controller 20 may control one or more actuators 10. In this example, a single wireless controller 20 controls a plurality of actuators 10, specifically seven actuators. This is advantageous for power management given the practical energy limitations of wireless power harvesting with this form factor device. Power management may include switches 60 independently controlled by controller 20 such that only one actuator is actively energized at any given time, such as with the other six switches effectively in an open state to electrically isolate the actuators. This can be achieved by rapid cycling of the actuators in a manner that is faster than the reaction of the mechanotranducers so that an individual experiences a physical sensation that all the actuators are on, even though they are rapidly cycling to reduce power demand. Other electronic components include diodes 70 and capacitors 80. FIG. 2 is a circuit layout, without the actuators and FIG. 3A labels the various components. FIG. 3B includes the seven actuators, specifically illustrating how a single NFC chip 20 may control multiple actuators 10 in a wireless manner and by wireless power harvesting.

Figure 4:
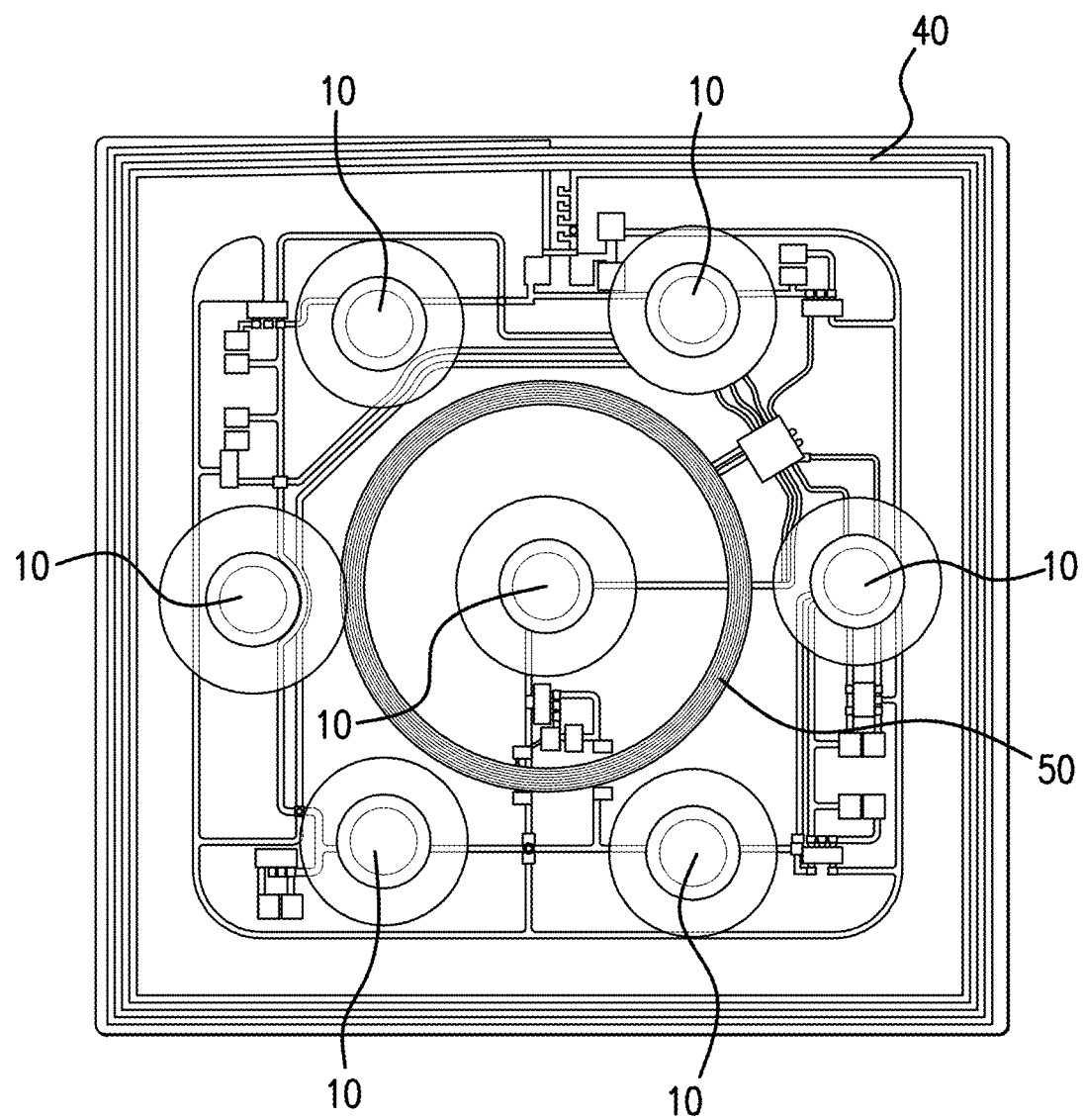
FIG. 4. is a photograph of an epidermal actuation device of FIG. 3B having the circuit layouts summarized in FIGS. 1, 2 and 3A. In this example, the actuators are vibratory actuators.
Figure 5:
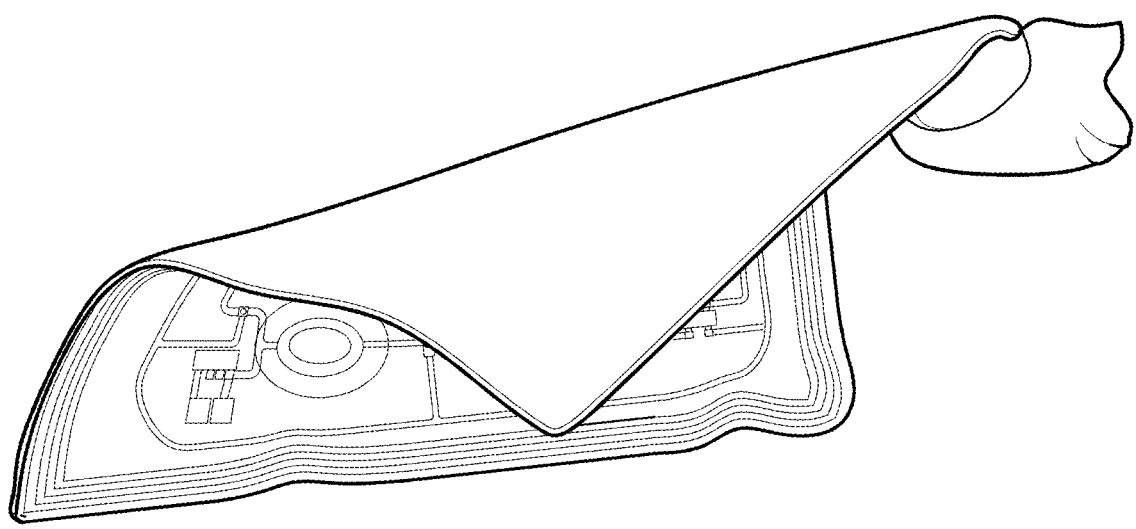
FIG. 5. Photograph of an epidermal actuation device illustrating the ability to accommodate bending without adverse impact.
Figure 6A:
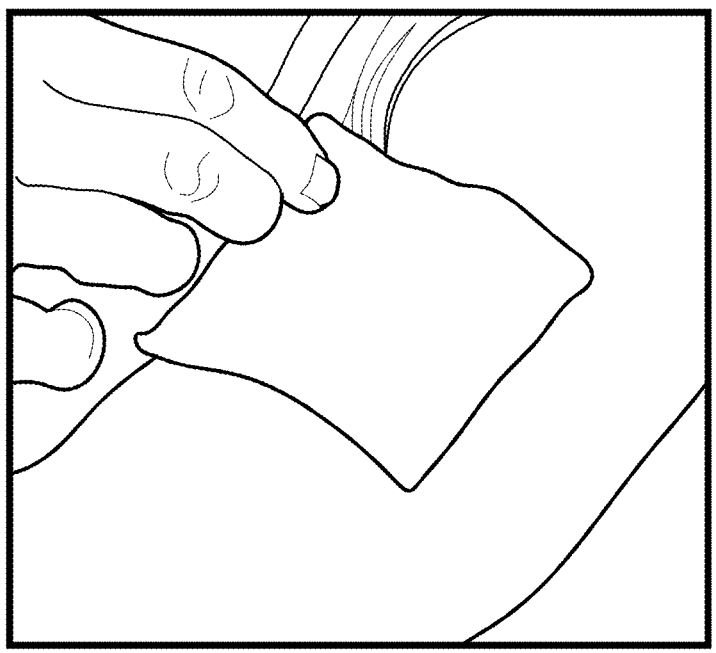
FIG. 6A is a photograph illustrating the epidermal actuation device may be characterized as soft and conformable to a biological tissue that is skin. The top and bottom panels illustrate device removal by peeling a corner away from the skin.
Figure 6A:
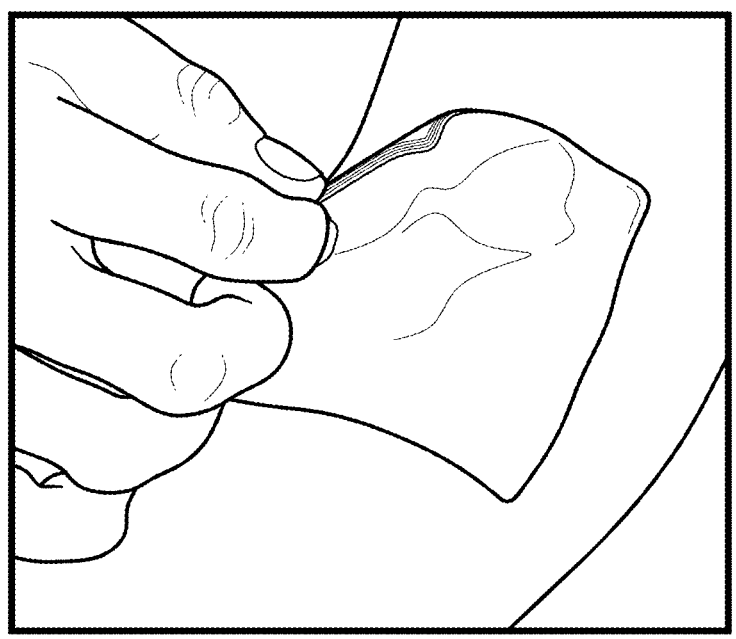
Figure 6B:
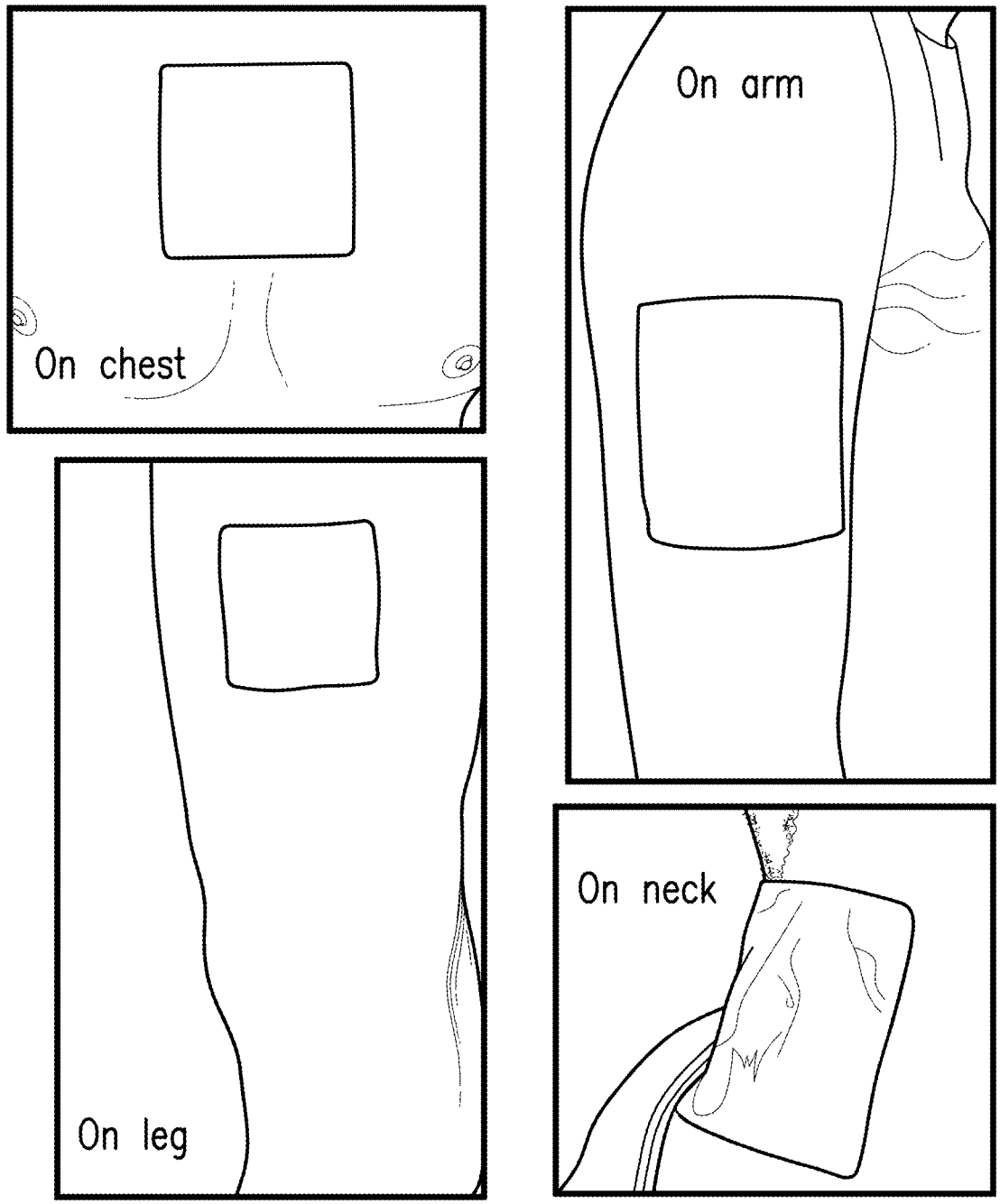
FIG. 6B illustrates the devices may be used anywhere on the body, including on the chest (top left panel), arm (to right panel), on the leg (lower left panel) and the neck (lower right panel). The devices are scalable to any size, depending on the application of interest.

FIG. 4 is an optical image of an epidermal VR device. The device fabrication may start from a 18 µm thick Cu coated polyimide (PI ~12.5 µm thick) sheet. Those Cu sheets are laminated on a PDMS coated wafer or glass slide (spin at 3000 rpm for 1 minute) handling substrate. The flexible Cu circuit board is patterned to two coils and connection wires/patches by wet chemical etching with Cu etchant through a hard baked mask of AZ4620 photoresist (PR). The photoresist is removed by rinsing of acetone. Here the design of the epidermal VR device, including a square shape large antenna coil 40 (3×3 inches, 7.62×7.62 cm) for power harvesting, and a circle shape small antenna coil 50 (diameter of 3.5 cm) for wireless communication. The large area antenna, accordingly, may be positioned around the periphery of the substrate, such as within the outermost 5% or 10% of the substrate dimension. The photo defined flexible Cu circuit board on the PI is spin-coated with another layer of PI as a Cu surface protection layer and hard baked at 250° C. in a vacuum oven for 75 minutes. The thin PI protection layer protects against oxidation of Cu surface, and also prevents scratching during device fabrication. Openings through the PI, formed by March RIE through a pattern of AZ4620 PR, provides access to the electronic parts/wire soldering with Cu contract patches. Then, the electronics elements, such as mechanical actuators, capacitors, resistors, electronic switches, and wireless controller (e.g., NFC chips) are soldered onto the Cu circuit board. These electronic parts, except for the mechanical actuators, are commercially available. The thickness of these parts are less than 1 mm. Next, the devices are encapsulated by pouring a small amount of low modulus PDMS silicone and then cured in a 70° C. oven overnight. The devices are carefully peeled off from the handling substrates and transferred to a silicone (Silbione®) coated spandex fabric cloth. The Silbione® coated fabric cloth are highly flexible and stretchable (up to 200% stretchability). The 3×3 inches device comprises 7 mechanical actuators. The overall thickness of the actuator device is less than 3 mm, with a weight of about 30 g. As illustrated in FIG. 5, the device may be bendable and soft, to facilitate conformability to the epidermis or skin (FIGS. 6A-6B).

Figure 7:
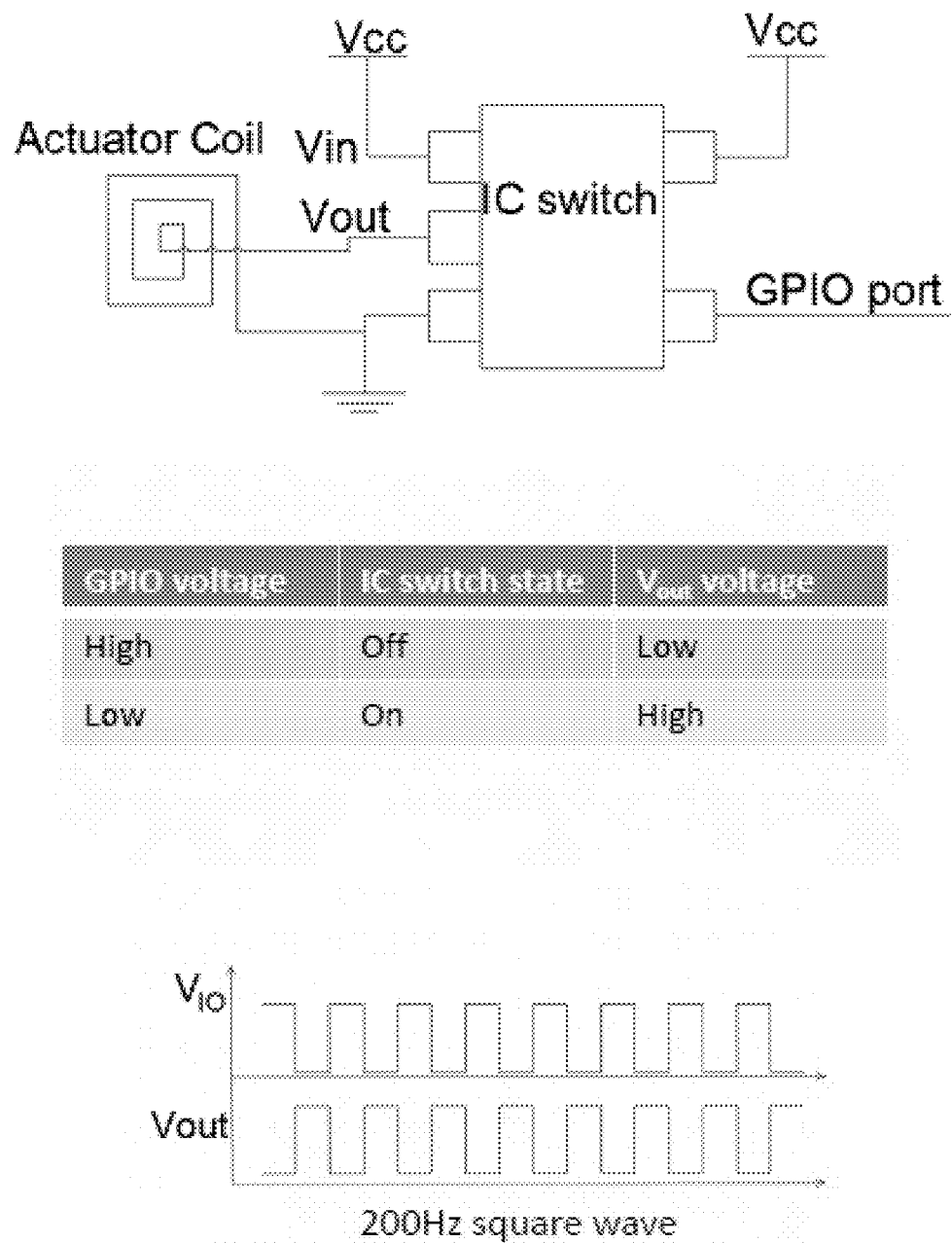
FIG. 7. The use of IC switches facilitates power of multiple actuators with a single chip that rapidly controls the IC switch state for multiple actuator switches (IC switch) in a scanning-type manner so that an individual experiences a feeling of simultaneous actuation of all actuators in the device even though only a single actuator receives power at any given time.

FIG. 7 illustrates the detail of an IC switch. The exemplary switch is shown with 5 ports that are connected to large, small antennas, and actuators: $V_{out}$ and ground ports connect to the two terminals of the mechanical actuator Cu coil, one $V_{cc}$ port close to the $V_{out}$ connects to the large coil as $V_{in}$ for power supply to mechanical actuators, the other $V_{cc}$ port connects to the $V_{cc}$ of TI NFC chip (wireless controller) on the small coil, as controlled $V_{cc}$, the last port connects to the GPIO port of the NFC chip. When the GPIO port provides high voltage, the switch is turned off, thus the output of the actuator is off. In contrast, the output of the actuator is turned on when the voltage of GPIO port are low or zero (see middle and lower panels of FIG. 7). Since the GPIO ports are programmed with specific frequency, the mechanical actuators vibrate under these frequencies. These actuators can work individually by switching the GPIO control ports. The switching time from one actuator to another for the current devices is less than 0.1 s.

Software programming and actuator control: As mentioned previously, the vibrations are generated by the vibrating magnet, which in turn vibrates because of the magnetic field induced in the coil. For example, it can be achieved by applying a 200 Hz square wave to the coil from RF430FRL15xH NFC ISO 15693 Sensor Transponder (Texas Instruments).

The NFC chip is programmed using Code Composer Studio (CCS) to generate this signal. This is done by alternating the output, of the GPIO (General Purpose I/O) Port, between HIGH & LOW. The chip's in-built timer is used to obtain the required frequency. In built system frequency utilizes sub-main clock (SMCLK), 2 MHz. Thus, possible frequency of square wave ranges from 0 to 1 MHz (approx.). A single NFC chip functions 8 GPIO ports, and each GPIO port can be independently programmable. Of course, chips having higher numbers of ports are readily incorporated into the devices described herein. Examples for vibrating sensors; a single transponder with a single actuator, and a single transponder with multiple actuators.

The NFC chip's program also incorporates an interrupt mechanism, which acts as the control for the square wave generation. This interrupt can be triggered by writing a specific hexadecimal value in a particular register resulting in the GPIO port outputting the square signal. The interrupt can be disabled by writing any other hexadecimal value in the same register. Thus, the interrupt acts as the control mechanism for the square wave. Such hexadecimal commands transfer via NFC Data Exchange Format (NDEF) Messages.

The necessary NDEF messages are written into the NFC chip using the RF Reader. The RF Reader may be FEIG's ID ISC.LRM2500-A which operates at 13.56 MHz. Its output power ranges from 2 W to 12 W and it can communicate to a computer via USB port. The latter is utilized to control the writing process using the RF Reader with a custom GUI. The GUI displays the connection status of the RF Reader with the computer. If the status is disconnected, a button can be pressed to re-establish the connection. Once the RF Reader is connected to the computer, the Initialize button can be used. This currently sets the RF power is between 4 W to 12 W. The feature to alter the power choosing the desired power can be added to the GUI. If a dynamic antenna is used, the feature to auto tune the antenna can also be incorporated.

Once the system is initialized, the inventory button is used to obtain the Tag ID's of all the NFC chips in the field. These ID's are listed in a drop-down menu, which can be used to select the desired NFC chip. The ON & OFF buttons can then be used to switch on & off the selected device. Time delay is inevitable when commanding ON & OFF for transponders via RF reader, because RF reader is limited in sending each command to 25 ms. For instance, manual operation (ON & OFF) of an actuator where clicking ON & OFF buttons manually will result in 50 ms delay until the next actuator operation.

Figure 8:
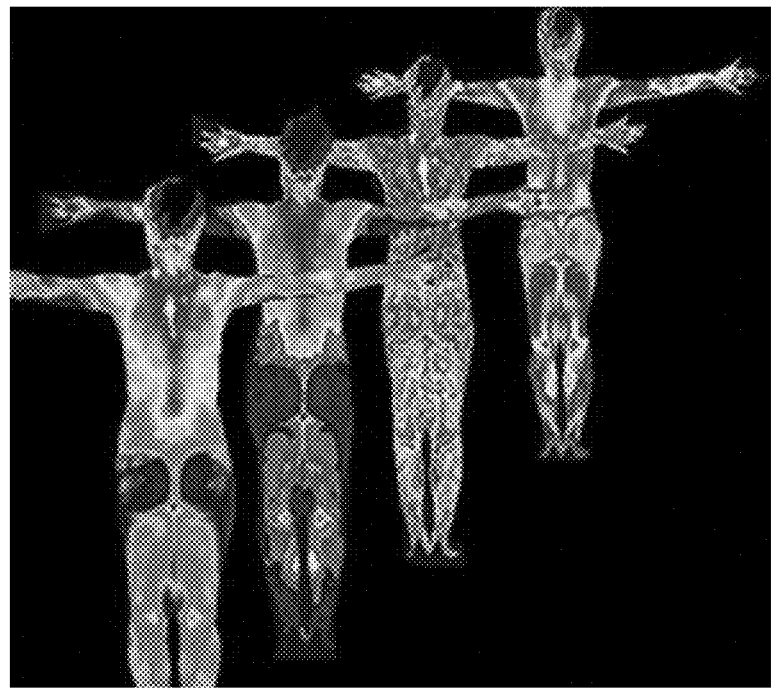
FIG. 8. Illustration that any of the devices provided herein may be used for up to full-body actuation and/or sensing, including in an epidermal virtual reality application. The four images of a person on the top panel schematically illustrates a color map of a physical parameter sensed on a person's skin surface as a function of time. Such an image is also compatible with a distribution of actuators activated so as to achieve the color map. In this manner, the individual may feel a virtual force from another person (e.g., a third-person touch onto the person), a force exerted on another person (e.g., the person touching a third-person or another surface), and/or heat. The bottom panel illustrates a plurality of biologically interactive devices, with two-way communication with an external controller (e.g., a computer, smart phone, etc.).
Figure 8:
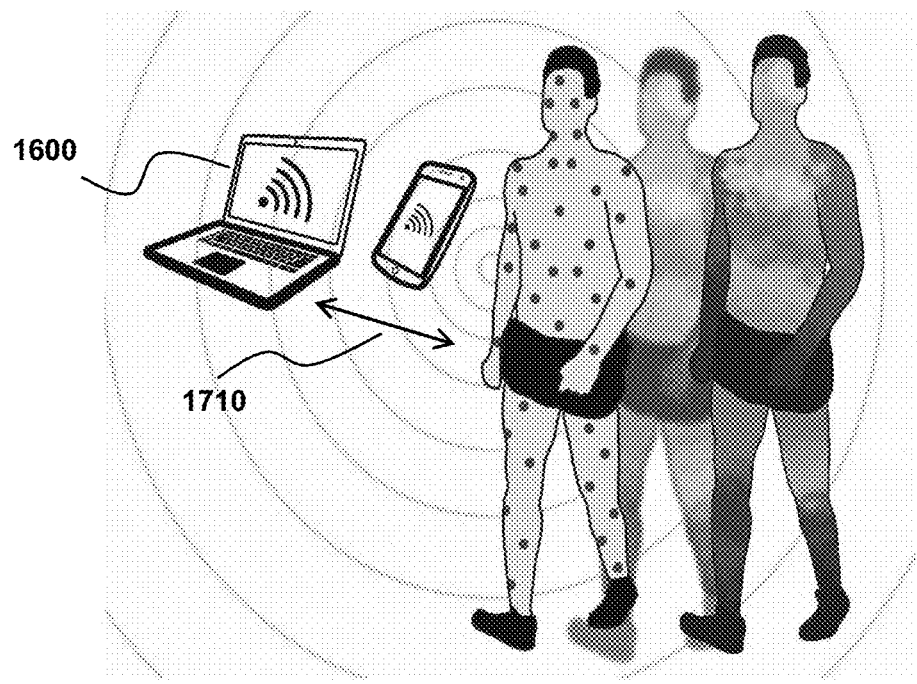

FIG. 8 exemplifies an epidermal VR application, relying on highly stretchable/flexible devices with various kind of actuations, including mechanical, thermal, etc. These devices may be laminated or temporarily "tattooed" on any part of the skin (see, e.g., FIG. 6B), up through to whole body, from head to feet. All these actuators are wirelessly controlled and powered. Accordingly, individuals feel "touch", "punch", "heat", etc. when playing games, video communicating, or the like, without being physically constrained by hard-wires to external components.

Figure 9:
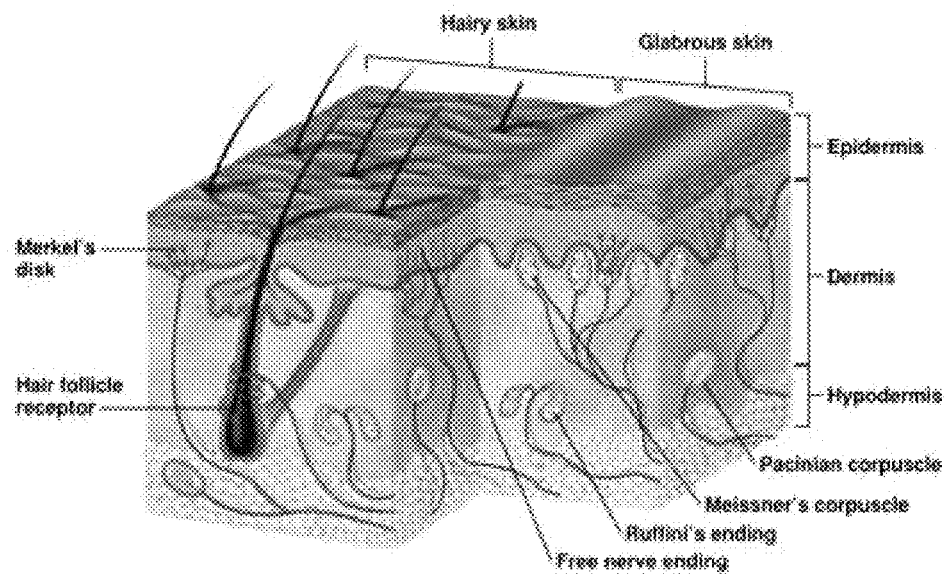
FIG. 9. The top panel illustrates relevant mechanoreceptors of the human epidermis/dermis/tissues and relevant nerves. The bottom table summarizes relevant sensing modalities and corresponding frequency ranges for the various mechanoreceptors. For sensing touch, for example, 200 Hz may be the most intensely sensed frequency, where that frequency application is felt by the body as a firm touch. More subtle squeezing type pressure tends to be generated with lower frequencies.
Figure 10:
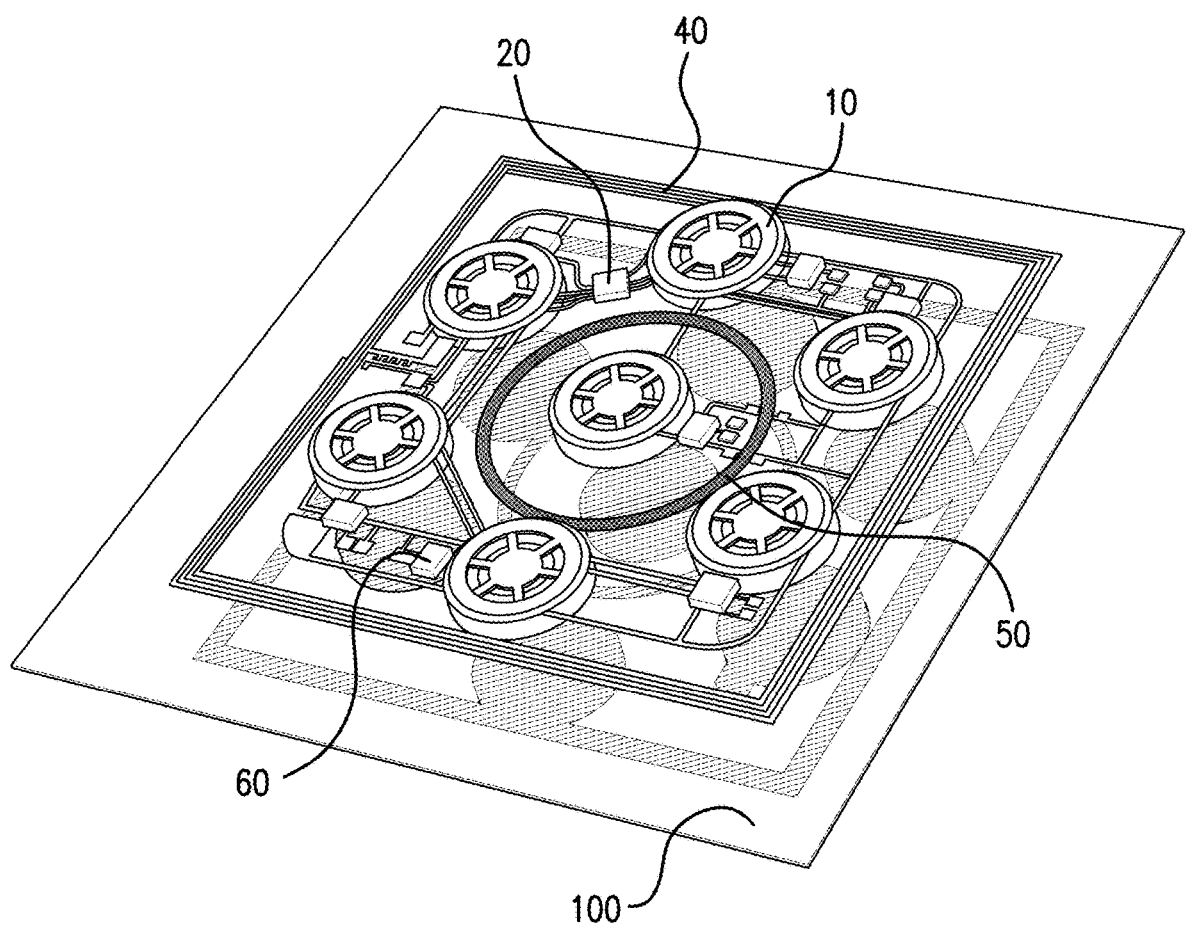
FIG. 10. Schematic illustration of a representative device suitable for epidermal virtual reality applications.

Referring to the mechanoreceptors of human epidermis/demis organ/tissues, Meissneer's corpuscles and Pacinican corpuscles (FIG. 9) are the most sensitive parts. They are responsible for the sensing of vibration with sensitivity as high as several micrometers deformation amplitude on skin, when the vibration frequency is about 200 Hz. So, the generation of a 200 Hz pulse actuation is an important physical parameter to consider for the mechanical actuators. Other frequency ranges are relevant for other mechanotransduction regimes and sensing modality. For example, a frequency less than 40 Hz is typically felt as a "touch, press", with a strong strength actuator required to mimic this touch. At greater than 40 Hz, texture can cause human's skin to feel vibrations, with the main range for those vibrations from 40 Hz to 300 Hz. For reference, frequency of vibration of a motor in a cell phone is typically greater than 55 Hz A representative design of an epidermal VR device, including a large antenna coil 40 for power harvesting, and a small antenna 50 coil for wireless communication, is provided in FIG. 10. The actuation system is fabricated on a highly stretchable substrate 100, to facilitate conformal coated on skin and robust function, even under large skin deformation. A NFC chip 20 may be used in the system for communication and wireless control. Numbers of actuators 10, antenna coil dimensions, and relative spacing, for example, can be varied depending on body mounting area and application of interest. The large antenna coil may function as a wireless power supply, the small antenna coil as a wireless control "remoter". The small coil electronically connects with a NFC chip, and the chip can control multiple actuators. The actuator device may be supported by an ultra-flexible substrate 100, such as a fabric, polymer, rubber, soft plastic, or the like. Although the example illustrates seven spatially distributed, any of the size of the coil, actuator number, relative positioning of the electronic components, can be varied, including depending on body mounting area and application of interest.

Figure 11:
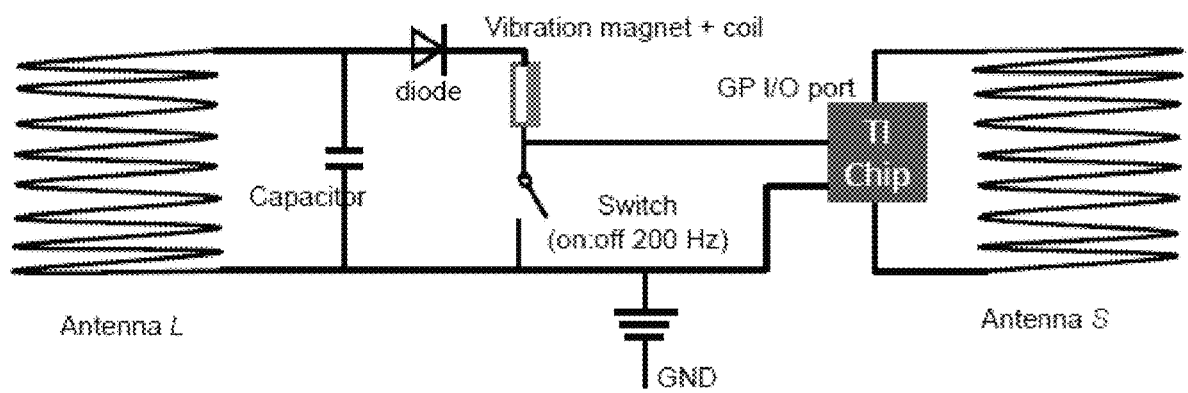
FIG. 11. Circuit diagram schematic of the actuator and associated electronics for powering and wireless control and communication.

FIG. 11 shows an embodiment of a device circuit and electronic diagram, including for epidermal VR applications. Energy harvesting part-large coils are connected with capacitors, resistors, diodes, in parallel or in series to optimize the generated RF power from a giving antenna (Antenna L). The power generated by a 3×3 inches square coil ranges from 30 mW to 120 mW, with a giving antenna power of 4 W to 12 W (calculated based on a 5 cm working distance between devices and power giving RF). Small coils are connected to wireless controller chips, such as TI NFC chips; each NFC chip has a plurality of output/control parts;

in this exemplified embodiment, 8 output/control ports (GPIO ports), which control the on/off of various actuators, including by control of switches. For simplicity, FIG. 11 illustrates a single actuator/switch pair. The vibration frequency may be controlled from between 0 Hz up to 500 Hz, with typically 200 Hz vibration used with humans due to human skin mechanical receptor properties. The GPIO ports of NFC chips are programmed with a certain frequency signal, to control a switch on and off state. Alternatively, a 200 Hz signal can be generated by integrating oscillators that are able to convert DC power to a 200 Hz (or any other desired frequency) signal (see, e.g., FIG. 12). The switch connects with GPIO ports, large antenna coil, and actuators, illustrated in this example as a mechanical actuator. Of course, any type of actuator may be incorporated into the circuit, including thermal, pressure, chemical, or other actuator selected dependent on the physical response desired. Antenna L (Larger): power supply, much higher power than those for powering the chips, with power determined by RF power, coil size etc. Antenna S(Smaller): control part, program multiple GP I/O ports to control 200 Hz on/off of the switch, each port connect with one device. The antennas L and S may share one RF, both of them working at 13.56 MHz.

Figure 12:
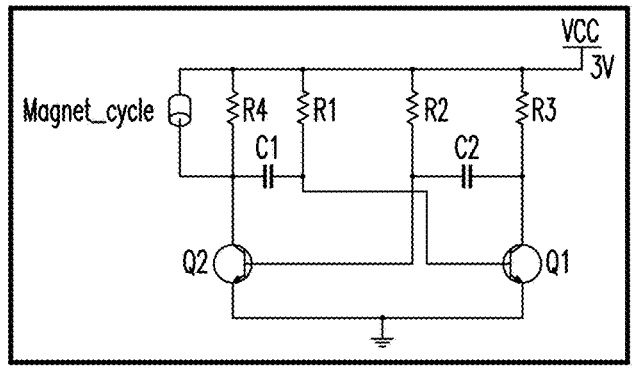
FIG. 12. Oscillator circuit design examples useful for controlling a vibratory-type actuator. In this manner, the oscillation frequency is readily adjusted by changing the value of capacitors and/or resistors.
Figure 12:
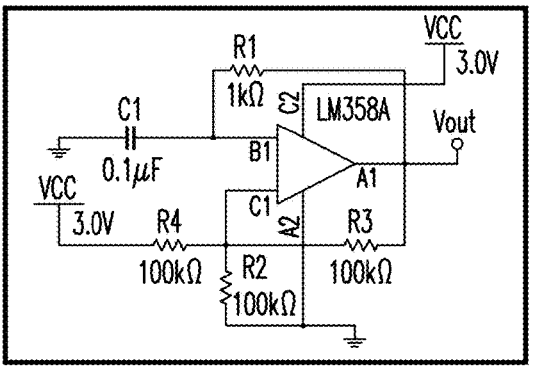
Figure 12:
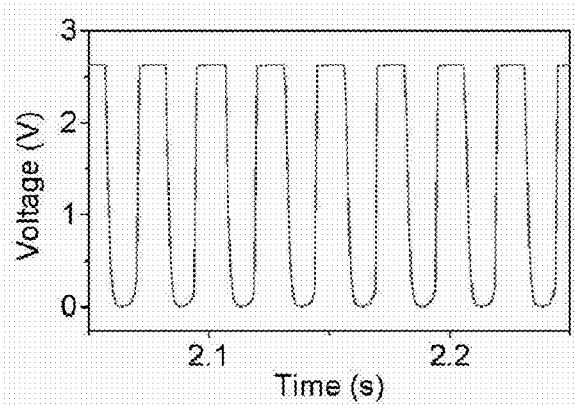
Figure 12:
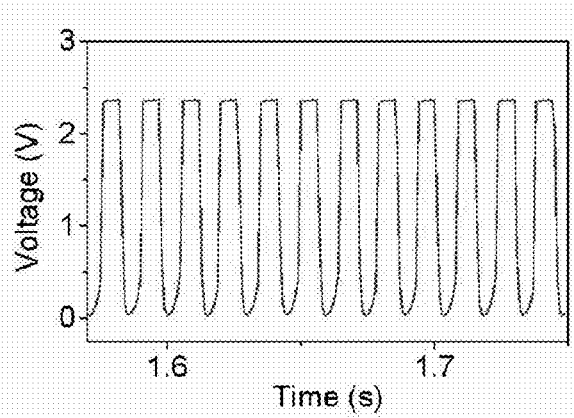

FIG. 12 illustrates two representative designs of oscillators. The oscillation frequency can be adjusted by the changing the values of capacitors and/or resistors. In this manner, DC power is converted to, for example, a 200 Hz output useful for controlling mechanical actuators.

Figure 13:
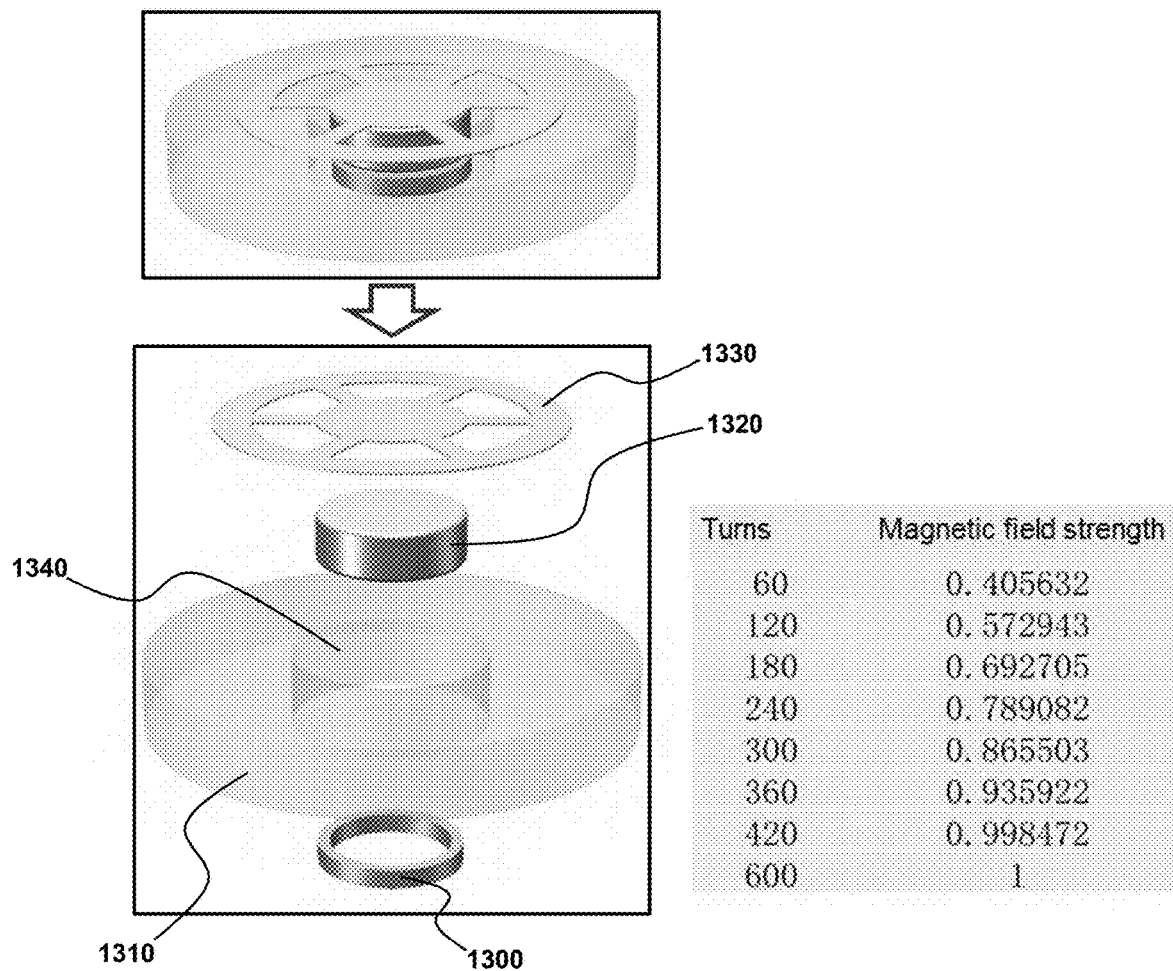
FIG. 13. Schematic illustration of an exemplary mechanical actuator. The left panels illustrate mechanism of vibration by use of an electrically-conducting coil and magnet positioned in a cavity within a soft and deformable material, such as PDMS. The right panel illustrates magnetic field strength variation with number of coil turns.
Figure 14:
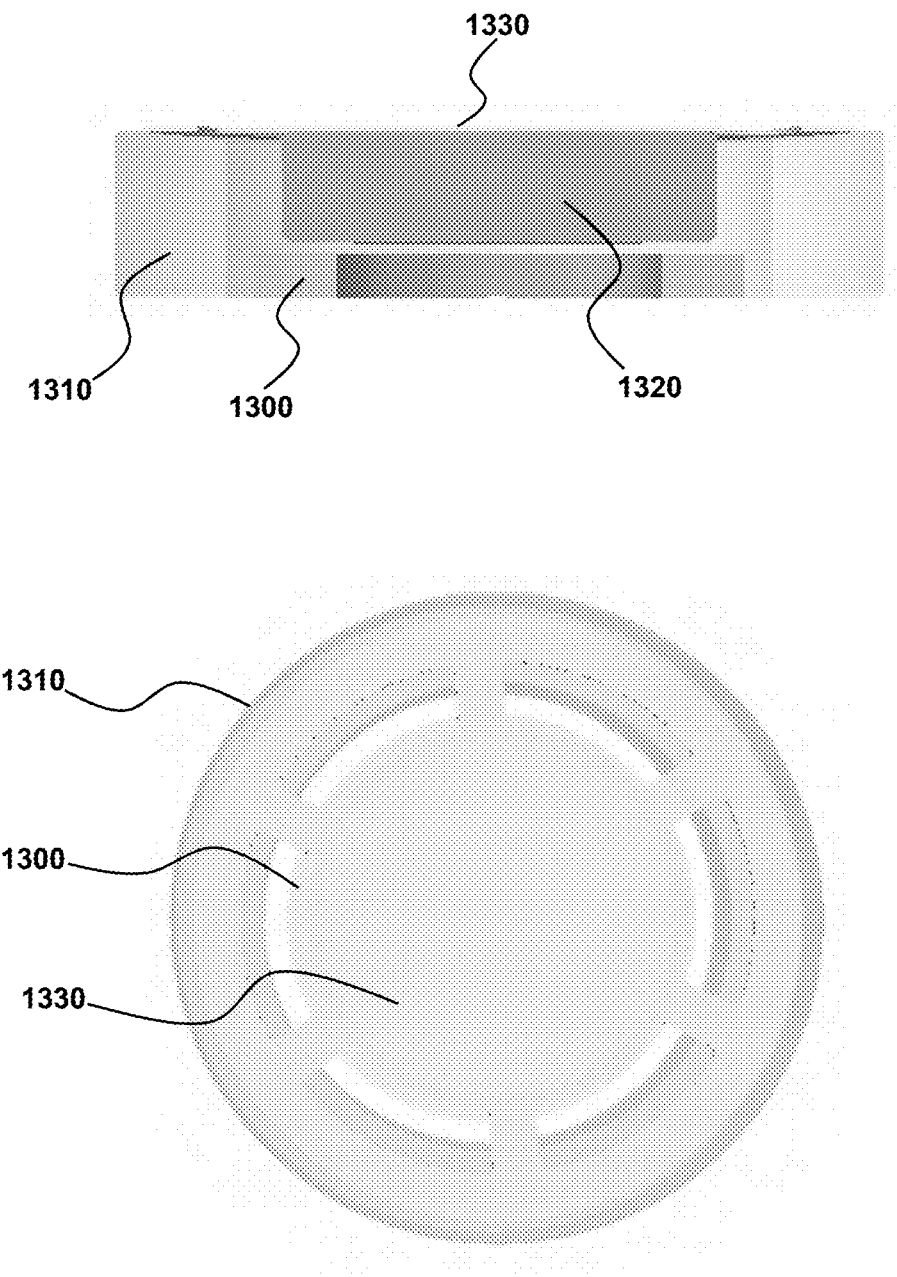
FIG. 14. The top panel is a side-view and the bottom panel a top view of the mechanical actuator of FIG. 13.

FIG. 13 is a schematic diagram of one type of mechanical actuator. The design is informed by numerical simulations using finite element analysis (FEA). In this example, the actuation means is by a Lorenz force that facilitates controlled vibration of a magnet in a dynamic magnetic field, ranging from 0 to 500 Hz. For example, the magnet may vibrate from a 200 Hz on/off magnetic field. The mechanical actuator may be formed from a Cu coil 1300, a ring shape mold made by a polymer layer (PDMS) 1310 with a recess 1340 having an inner diameter of 7 mm and overall PDMS diameter of 1 cm, and a permanent magnet disc 1320 with a diameter between about 3 to 5 mm and thickness between 0.5 to 1.5 mm positioned in the PDMS recess 1340. Once a dynamic voltage is input into the Cu coil, an on/off magnetic field under specific frequency is generated, thus, the magnet will vibrate via Lorenz force, thus the magnet vibrates at the selected frequency. According to FEA simulation and electromagnetic principles, increasing the turns of Cu coil increases the magnetic field strength. Considering the balance of Cu coil thickness and magnetic strength, we select about 300 turns winded Cu wires (50 μm) as the coil. Thus, the general configuration of the actuators in this example is a PDMS ring 1310, the bottom Cu coil 1300, and the top magnet 1320. The magnet is fixed by a photo/March RIE defined thin PI layer 1330 (12.5 μm) to maintain a small gap of ~0.3 mm from the Cu coil. The gap between magnet and coil can be selected so as to achieve maximum vibration. The overall thickness of the actuators are about 2 mm, with a weight of about 2.5 g. FIG. 14 provides a side-view (top panel) and a top view (bottom panel) of the mechanical actuator of FIG. 13.

Figure 15:
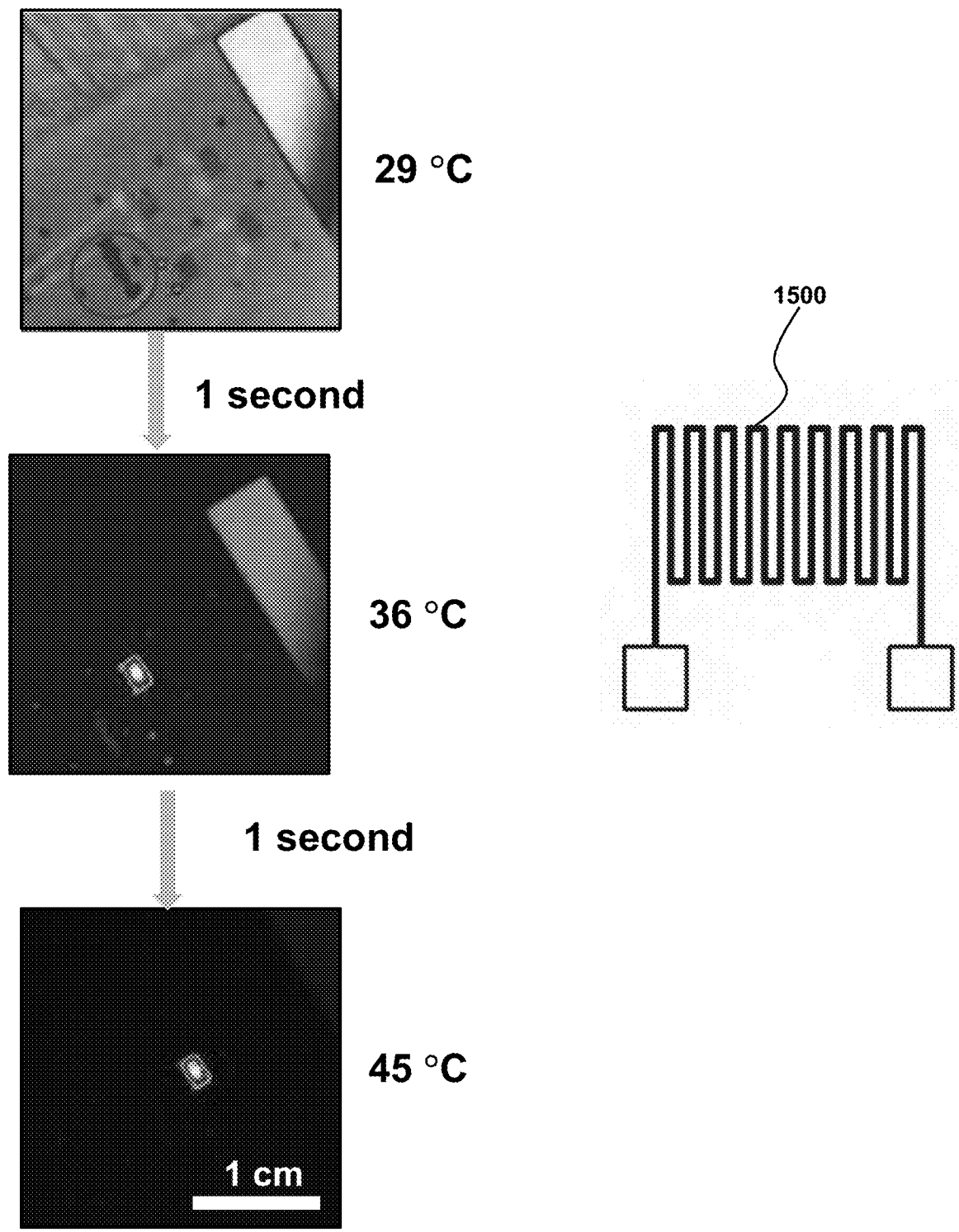
FIG. 15. The right panel is a schematic illustration of a thermal actuator and the left panels illustrate temperature change over time, including accommodating a temperature increase from 29° C. to 45° C. in 2 seconds. The heating area is approximately 3 mm×4 mm.

A thermal actuator 1500 is illustrated in FIG. 15. The heater may have a width of about 50 μm. Thermal actuation may rely on the same wireless power described for the mechanical actuator examples. The thermal actuators may fabricated using photolithography of e-beam evaporated 200 nm Au thin film. The pattern is a square shape with area of 3×4 μm, with a wire width of 50 μm. The temperature of these thermal actuators can increase rapidly, with the left panels illustrating an increase from 29° C. to 45° C. in a few seconds. In this example, a large antenna 40 directly powers the thermal actuator and generates heat by electrical resistance heating. the images on the left is a representative demonstration of thermal actuation and resultant temperature change, powered by a 3"×3" large antenna.

Figure 16:
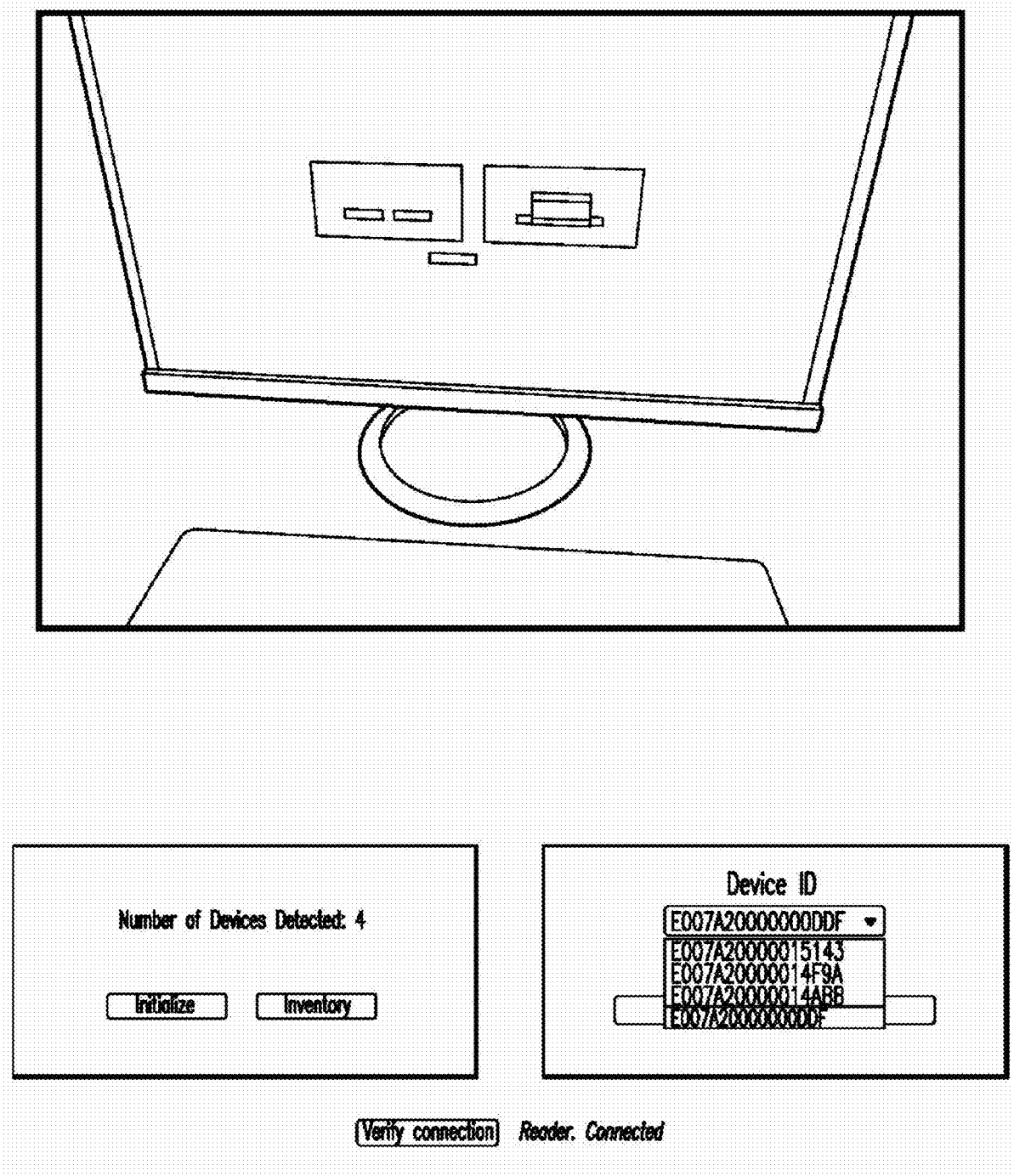
FIG. 16. Representative example of an external controller, including a graphical user interface for control of individual actuators via wireless communication, in this case four actuators. The actuators may be controlled in an on/off configuration independently.

FIG. 16 illustrates an external controller 1600, in this case embodied in a software control panel running on a computing device and visually displayed on a display. In this example, the device comprises four actuators and, from the software interface, each of the four actuators are identified and displayed in the external control platform via wireless communication. Those actuators can then each be controlled remotely via the interface, including turned on/off independently, remotely and wirelessly. The actuation system having 4 actuators are tested under a power giving antenna. A 200 Hz of vibration signal is confirmed. In this manner, virtual experience may be provided from a third-party during a video chat, game, or the like, to a remotely located person who is in contact with any of the actuation devices described herein.

Figure 17:
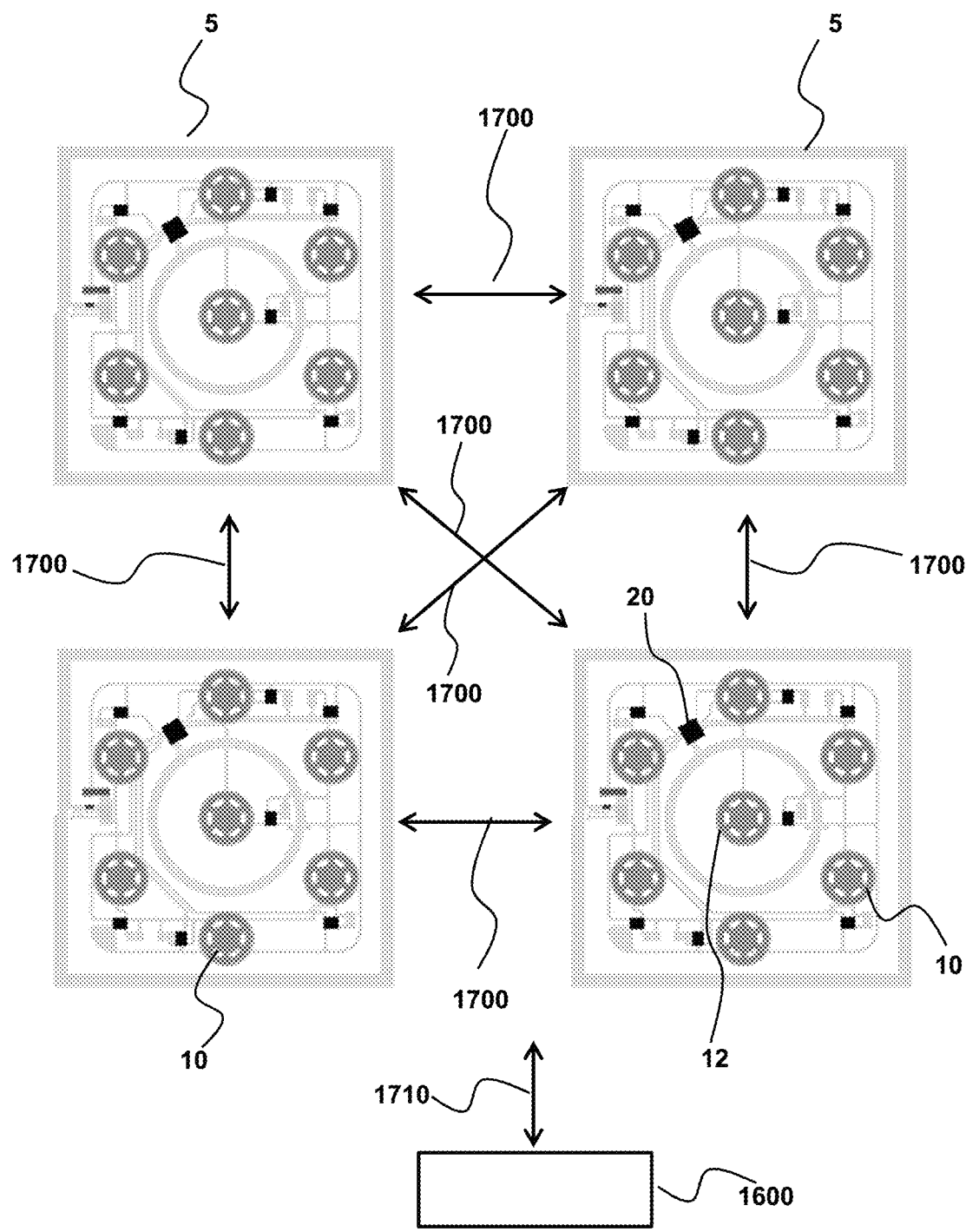
FIG. 17. Schematic illustration of the scalability of the devices described herein, with the ability to individually control actuators from within a large number and large area coverage.

The actuation devices provided herein are particularly suited for scaling, including by incorporating a plurality of the actuation devices in one system, wherein each actuation device comprises a plurality of spatially distributed actuators. For example, FIG. 17 schematically illustrates bi-direction communication between a plurality of the actuation devices 5 (also referred interchangeably as "biologically interactive devices"), with each actuation device 5 comprising a plurality of actuators 10 (exemplified as 7 actuators). The six double ended arrows 1700 emphasize bi-directional communication between the devices. In this manner, the status of one of the devices 5 may be used to affect a change in a different device 5. This aspect may be particularly relevant for actuator devices that further comprise one or more sensors 12. A physical parameter may be directly measured with sensor 12 and used to control another device 5 via transmission 1700. As described herein, external controller 1600 may provide uni-directional or bi-directional communication 1710 with an actuator device 5. For embodiments where actuator device 5 comprises both actuators 10 and sensors 12, the two-way or bi-directional communication 1710 with controller 1600 (either directly or indirectly via one or more wireless communication components), including with a NFC chip 20 provides versatile control and feedback to an individual remote from another individual. The two-way communication, of course, is also useful when both individuals are using an actuation device, with the ability to provide real-time on the fly feedback with sensors and/or actuation control. Even without such active feedback, the two-way communication is useful for presenting to the remote user confirmation of located and available actuators, along with the actuator device status of energized, off, or a value of the relevant actuation parameter (temperature, force, pressure, vibration frequency, electric field, optical, etc.). As needed, a higher capability component for wireless communication may be positioned near devices 5 to improve and boost communication capability without hindering the user.

Figure 18:
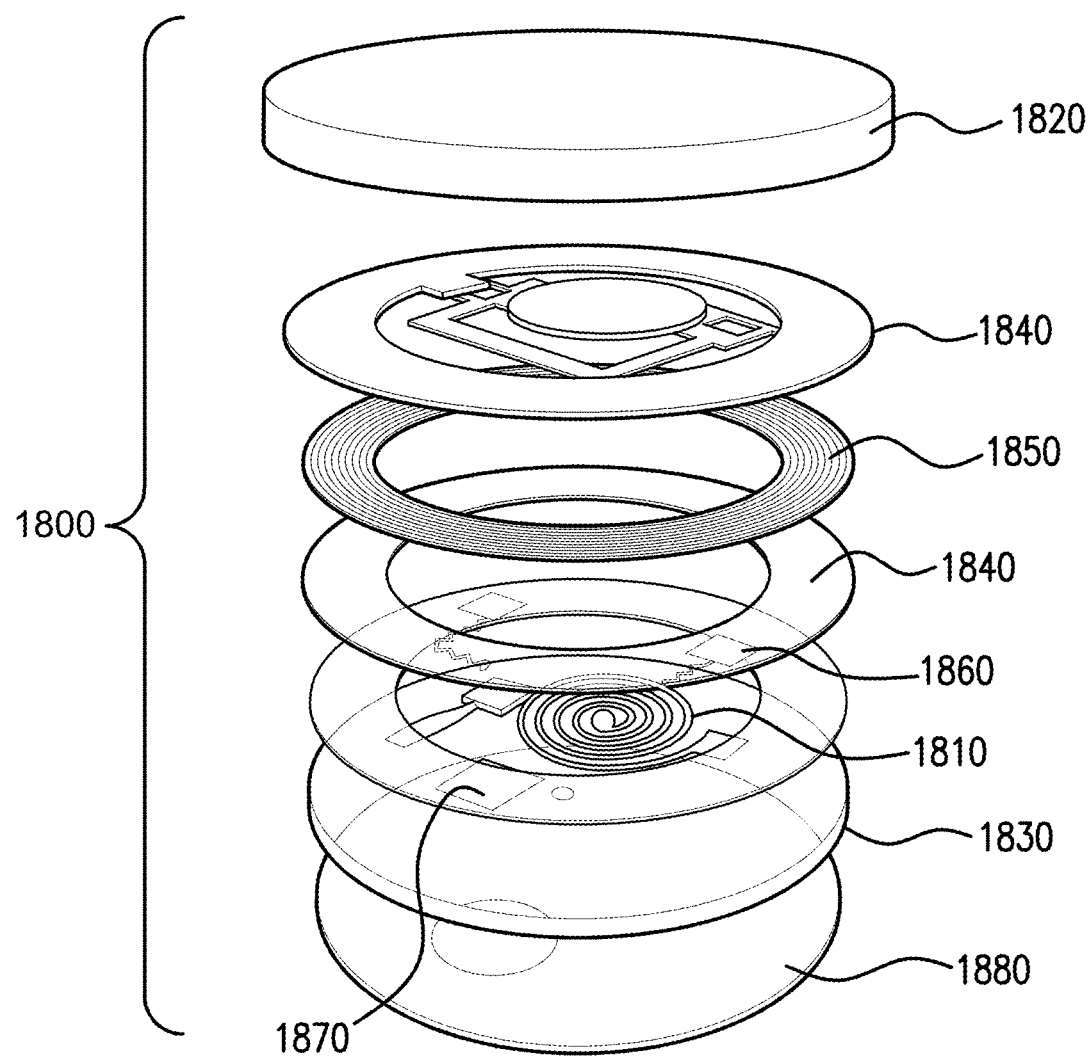
FIG. 18 is a schematic illustration of one type of a sensor, specifically a pressure sensor.

Sensors: The devices provided herein are compatible with a range of sensors. One exemplary sensor that is for measuring pressure is illustrated in FIG. 18. Pressure sensor 1800 may be a silicon pressure sensor formed from an ultrathin spiral shape layer 1810 of monocrystalline silicon. The pressure sensor may comprise a layer of silicon positioned between a top polymer layer 1820 and a bottom polymer layer 1830. Other components may include PI layers 1840, NFC coil 1850, bridge 1860, NFC chip 1870. An adhesive layer 1880, such as adhesive tape, may facilitate direct mounting to skin. Alternatively, as described herein, the sensor along with actuators may be incorporated into or on a substrate, with the entire device incorporated into, for example, clothing.

Figure 19:
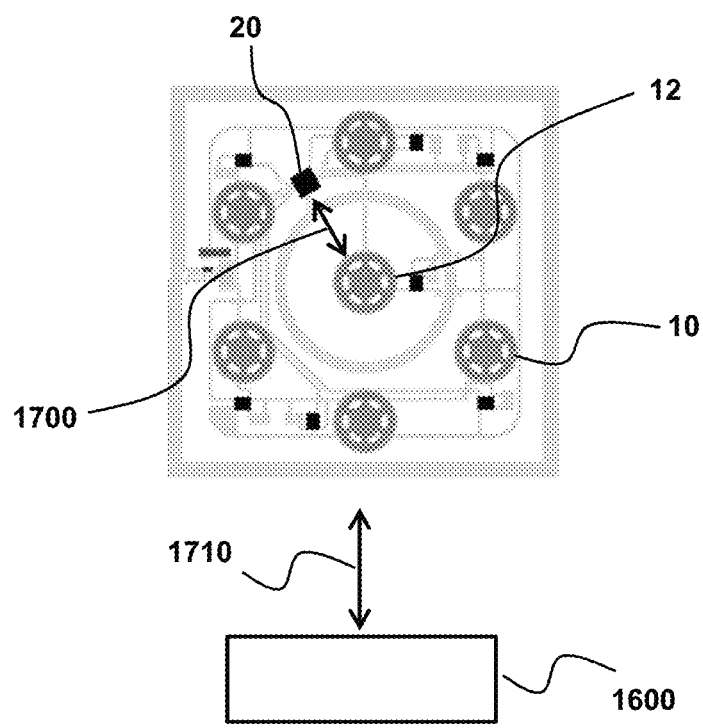
FIG. 19 schematically illustrates an actuator and sensor device, wherein the sensor is configured for autonomous actuator control in a feedback loop configuration to ensure a desired physical parameter sensed by the sensor on the skin is attained and/or maintained. The sensor may also function as a fail-safe to ensure actuators do not generate a physical parameter outside a safe level and upon approach of that level, the actuators may be automatically powered off.

FIG. 19 illustrates incorporation of a sensor in any of the actuator systems, including a biologically interactive device, to provide autonomous or semi-autonomous functionality. For example, external controller 1600 may provide unidirectional or bi-directional communication 1710 with an actuator 10 and sensor 12 device 5. Once an actuation signal is provided, sensor 12 may provide feedback control via communication 1900 with controller chip 20. In this manner the sensor may be used to independently measure a parameter of interest and used to further control actuations to ensure a desire level is reached. In this manner, the device is characterized as having autonomous or semi-autonomous functionality. For example, if the actuators or instructed by communication 1710 to generate a certain actuation level (e.g., temperature, pressure, or the like), sensor 12 may measure that parameter level in the tissue (e.g., temperature, pressure, or the like) and subsequently provide on-device command and control to controller 20 to ensure the an appropriate actuation level is imparted to the skin to achieve a desired parameter level in the skin. This is also a useful fail-safe, where actuation is stopped if there is an unwanted out-of-range parameter measurement, such as temperature, pressure or the like. A pressure sensor may be used to continuously measure pressure on the skin, and once a desired level of pressure for a desired level time is reached, the actuators may be powered off.

Example 2: Characterization of VR Devices

Figure 20:
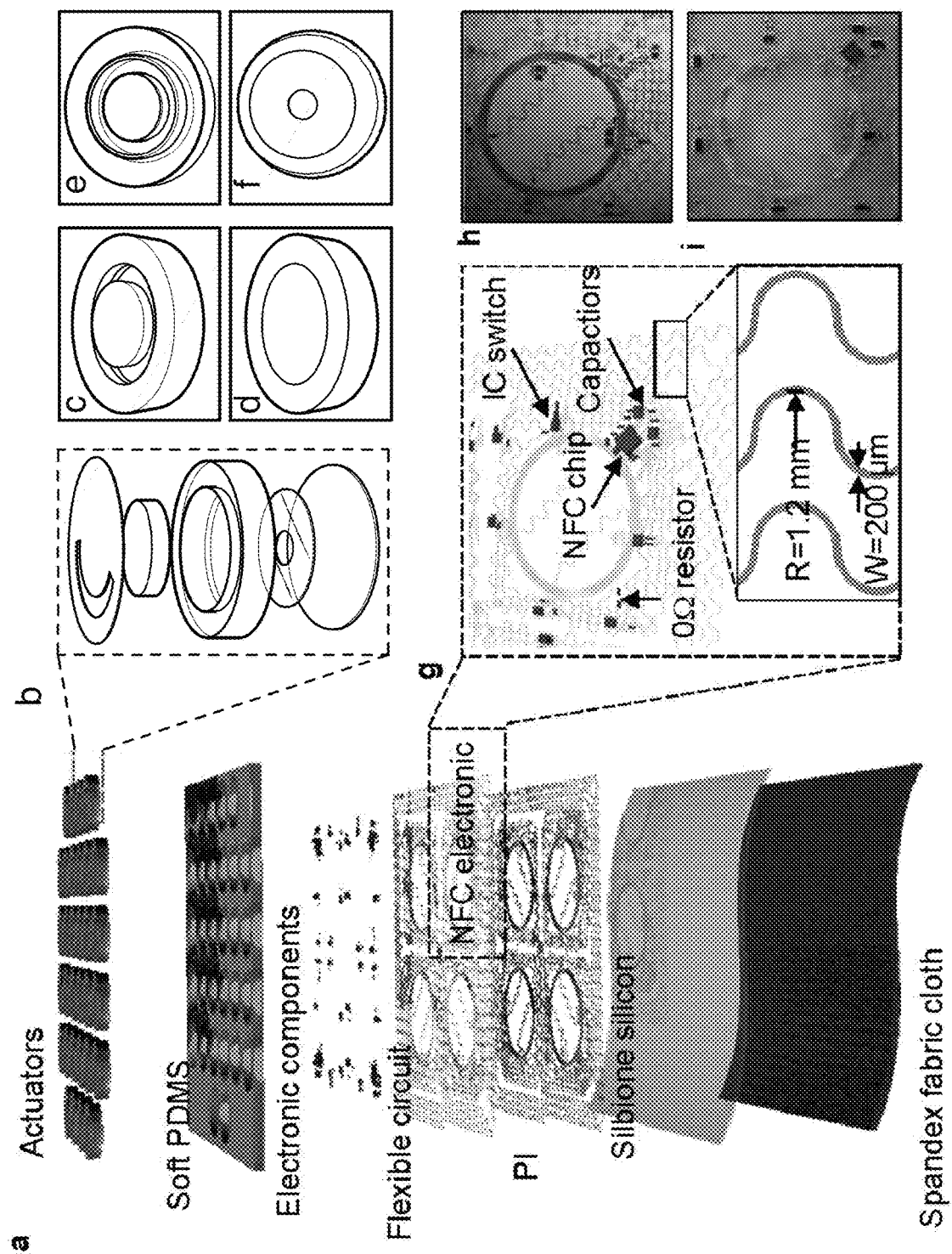
FIG. 20 is a schematic illustration and optical images of an epidermal VR device.

FIG. 20 illustrates an exemplary VR device. Panel a is an exploded-view schematic illustrations of an epidermal VR device with 32 mechanical actuators. The exploded view assists with visualizing the various components and layers, including the actuators (further illustrated in panels b-f), supported on a soft substrate (labeled as "soft PDMS") for facilitating comfortable conformal contact with the skin. Other illustrated components include the electronic components, flexible circuit, NFC electronics (further illustrated in panel g with images in panels h and i). Panel b is a schematic illustration of an actuator. Panels c and d are schematic diagrams of an actuator viewing from top (c) and bottom (d). Panels e and f are optical images of an actuator viewing from top (e) and bottom (f). Panel g is a schematic illustration of the NFC electronics with flexible Cu circuit. The inset shows a magnified view of the serpentine shape Cu coil. Panels h and i are optical images of a NFC coil before (h) and after integrating electronic components Device 2. The devices may be mounted on a biological tissue for additional characterization, along with bending, twisting and stretching characterization.

Figure 21:
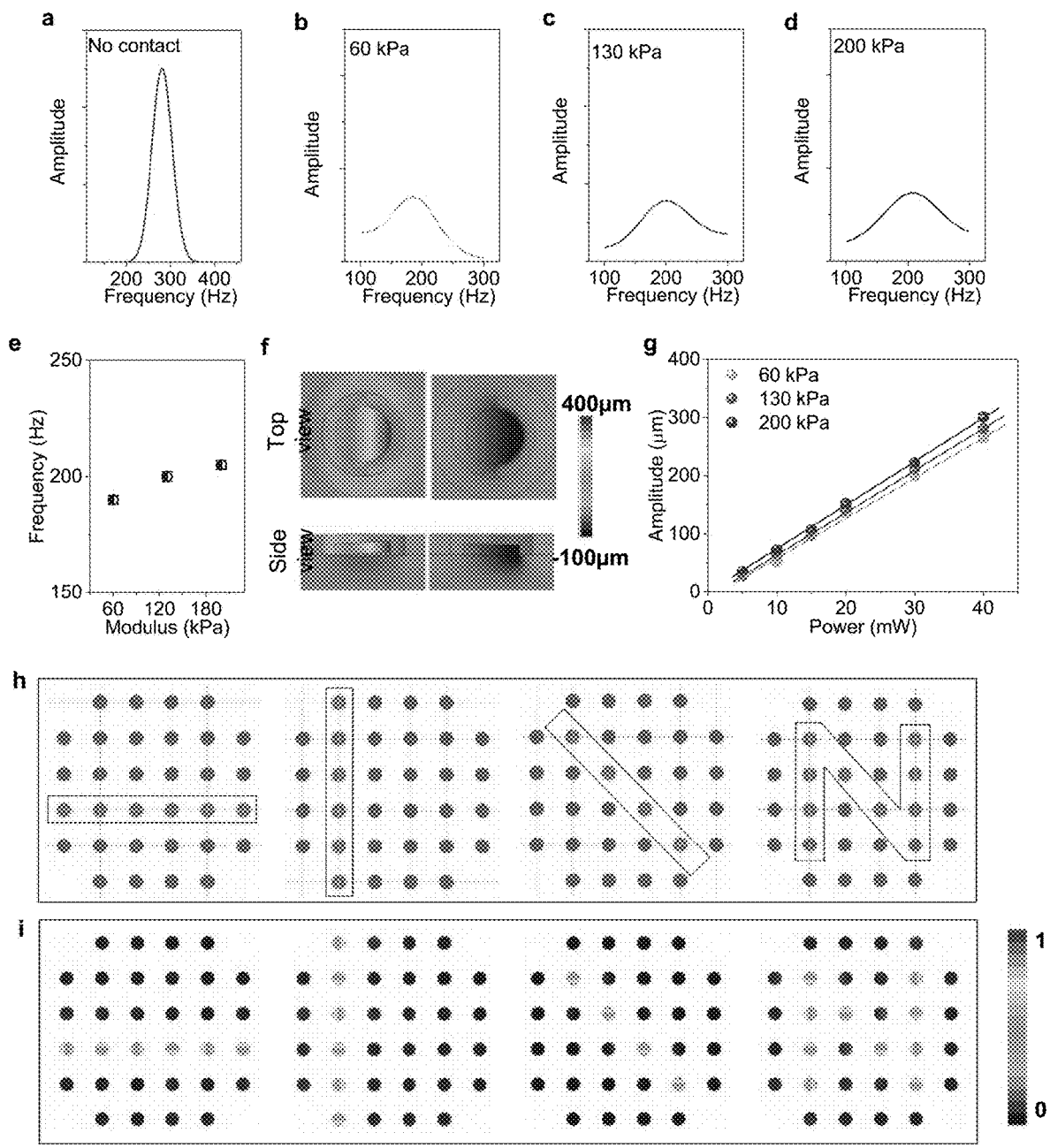
FIG. 21 summarizes an analysis of a mechanical actuator of an epidermal VR device.

FIG. 21 summarizes an analysis of a mechanical actuator. Panel a shows measured amplitude-frequency responses of a mechanical actuator without contact. Panels b-d shows measured amplitude—frequency responses of a mechanical actuator when contacting artificial skins of different stiffnesses: 60 kPa (b), 130 kPa (c), and 200 kPa (d). Panel e is resonance frequency of an actuator as a function of modulus of antiracial skins tested. Panel f is FEA results of the travel amplitude of an actuator in contact with skin, under an applied power of 40 mW. Panel g is travel amplitude of an actuator as a function of applied power. Panels h and i are schematic illustrations (h) and FEA (i) of mechanical coupling of actuators under various vibration patterns.

Figure 22:
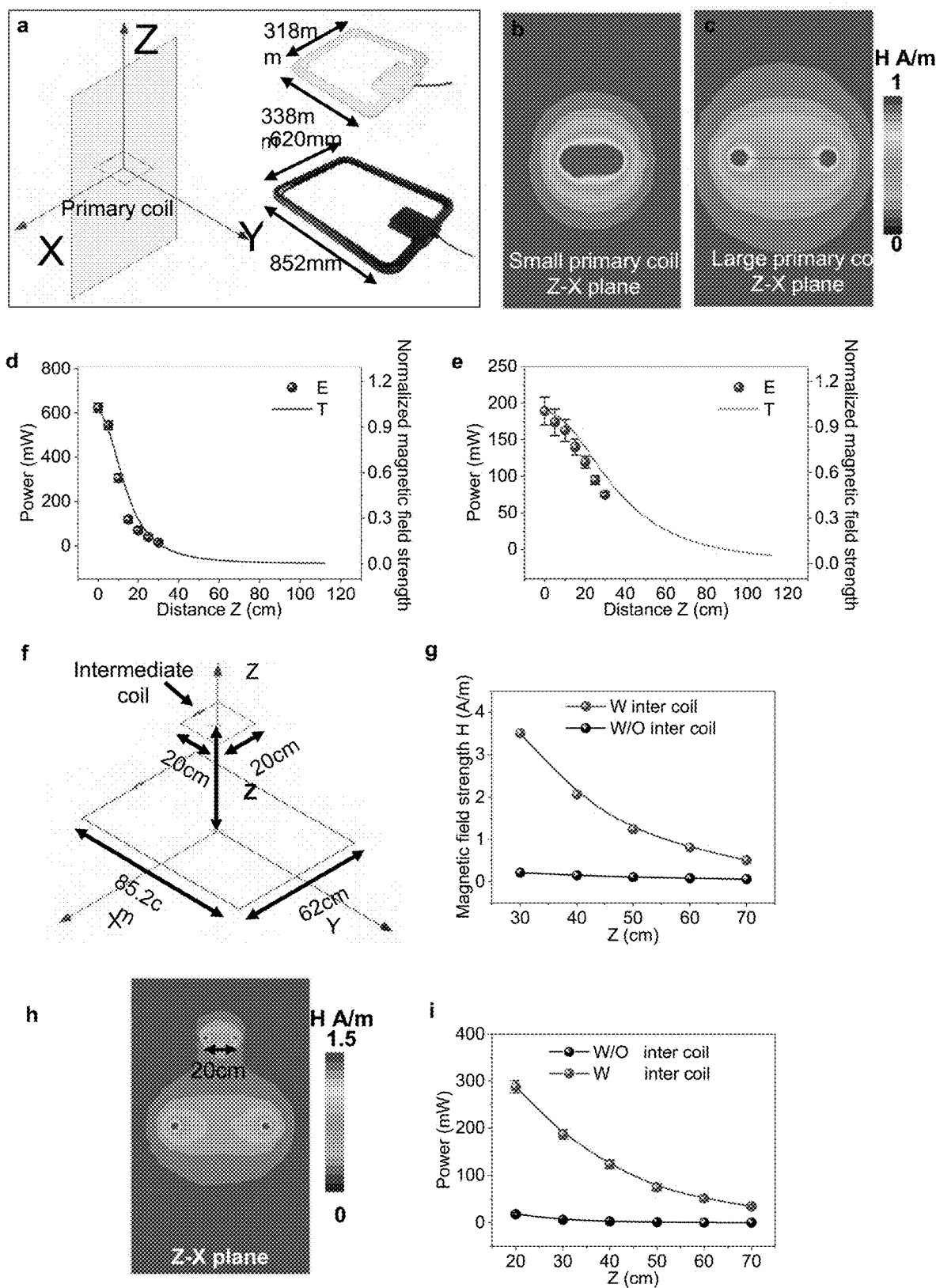
FIG. 22 summarizes an analysis of wireless power optimization of an epidermal VR device.

FIG. 22 illustrates wireless power optimization of epidermal VR devices. Panel a is a schematic illustration of a RF reader with 3 demission, and optical images of two RF readers, 318×318 mm and 620×852 mm, used in these demonstrations. Panels b and c are FEA of magnetic field strength of two RF readers versus distance of Z direction. Panels d and e are measured power of an energy harvesting coil of an epidermal VR device as a function of distance of Z direction. Panel f is a schematic illustration of an intermediate coil on top of a RF reader. Panel g is a simulated average magnetic field strength of an intermediate coil as a function of distance. Panel h is FEA of magnetic field strength of intermediate coil when it is on top of a RF reader. Panel i is measured power of an epidermal VR device as a function of the distance when the intermediate coil is introduced.

Figure 23A:
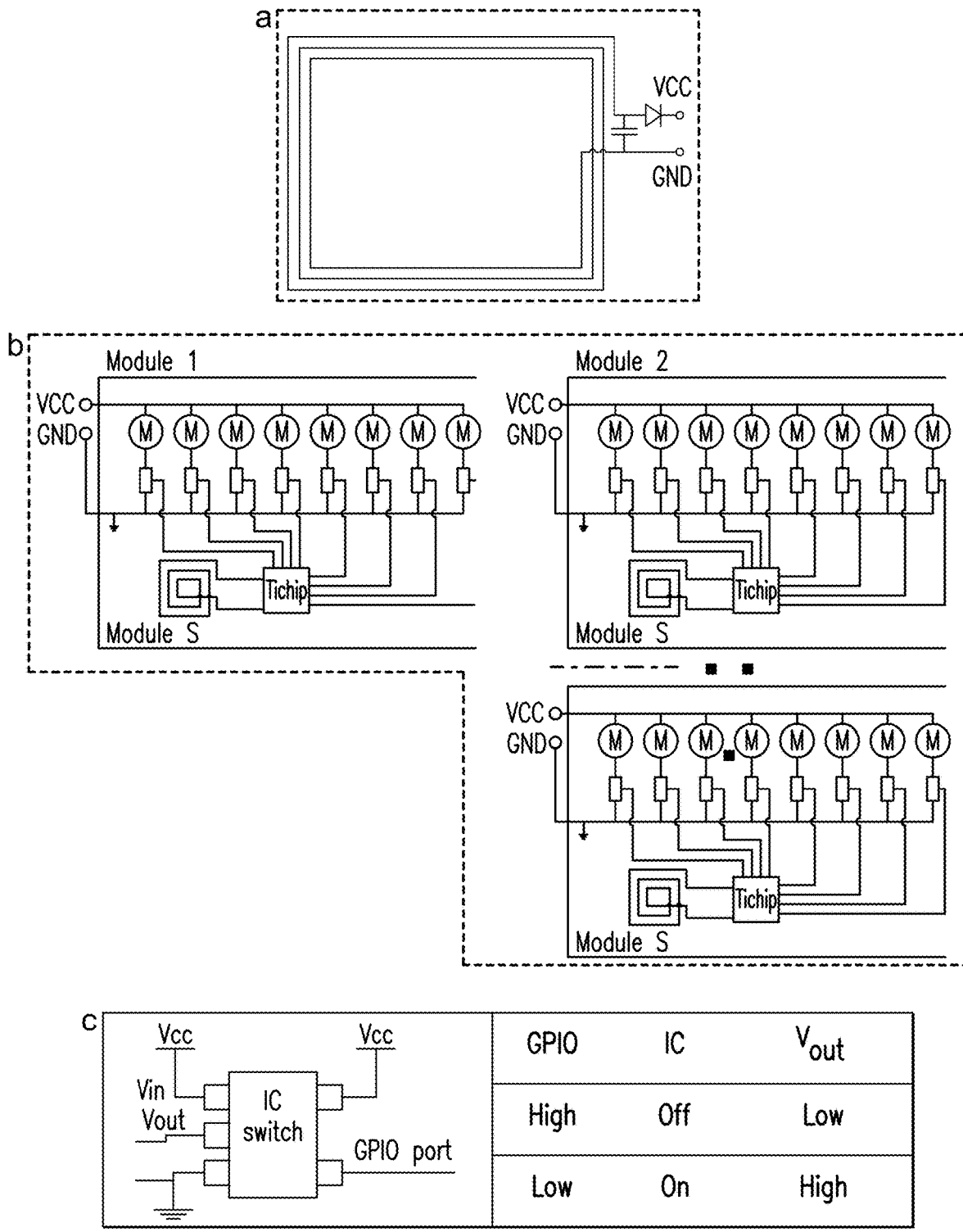
FIGS. 23A-23B provide a circuit diagram and characterization of a wireless operation system of an epidermal VR device.
Figure 23B:
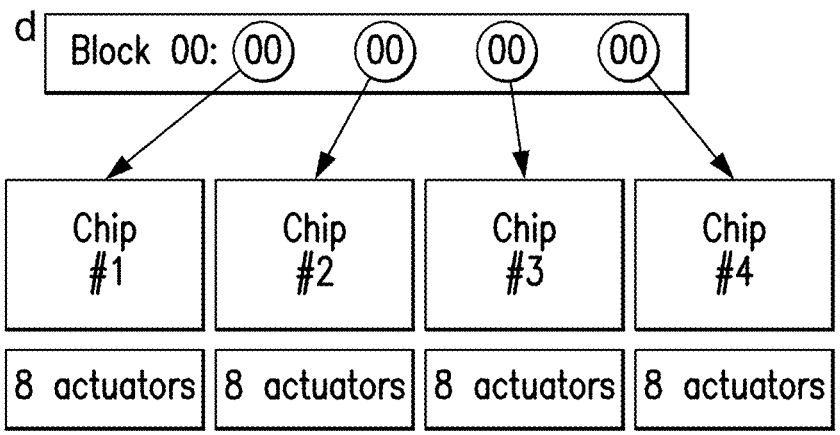
Figure 23B:
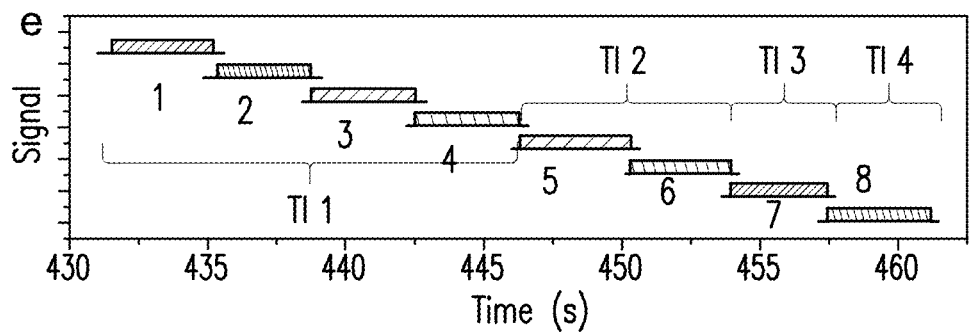
Figure 23B:
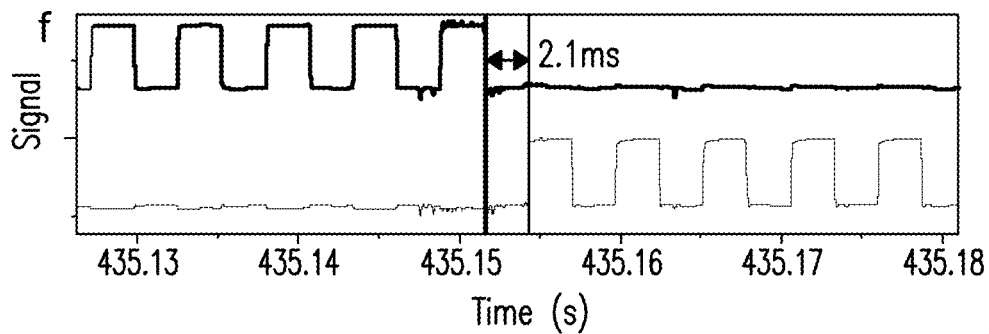
Figure 23B:
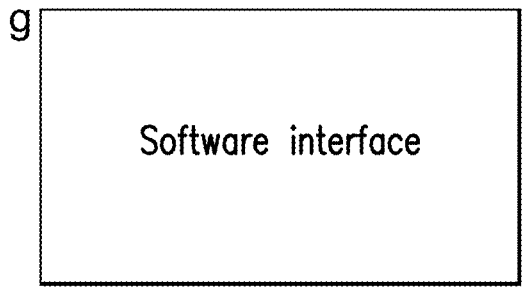
Figure 23B:
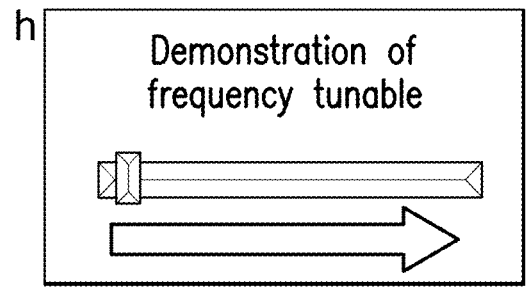

FIGS. 23A-23B illustrate a wireless operation system of the epidermal VR devices. Panels a and b are circuit diagrams of an epidermal VR device, with power harvesting coil (a), and several control modules (b), each control module has a NFC coil and a chip, 8 actuators controlled by 8 IC switches independently. Panel c is a schematic diagram of an IC switch, and the working principle of the switch. The output voltage of the IC switch is controlled by GPIO ports of NFC chip. Panel d is a working principle of command sending from the operation system. GPIO ports of each NFC chip is defined by two byte order, all actuators can be ignited in any form by portfolio of 8 bytes. Panel e is response time of actuators controlled by 4 NFC chips. Panel f is a magnified view of response time of switching from one actuator to another one. Panels g and h illustrates that a software interface may be used as part of the control system of epidermal VR devices.

Figure 24:
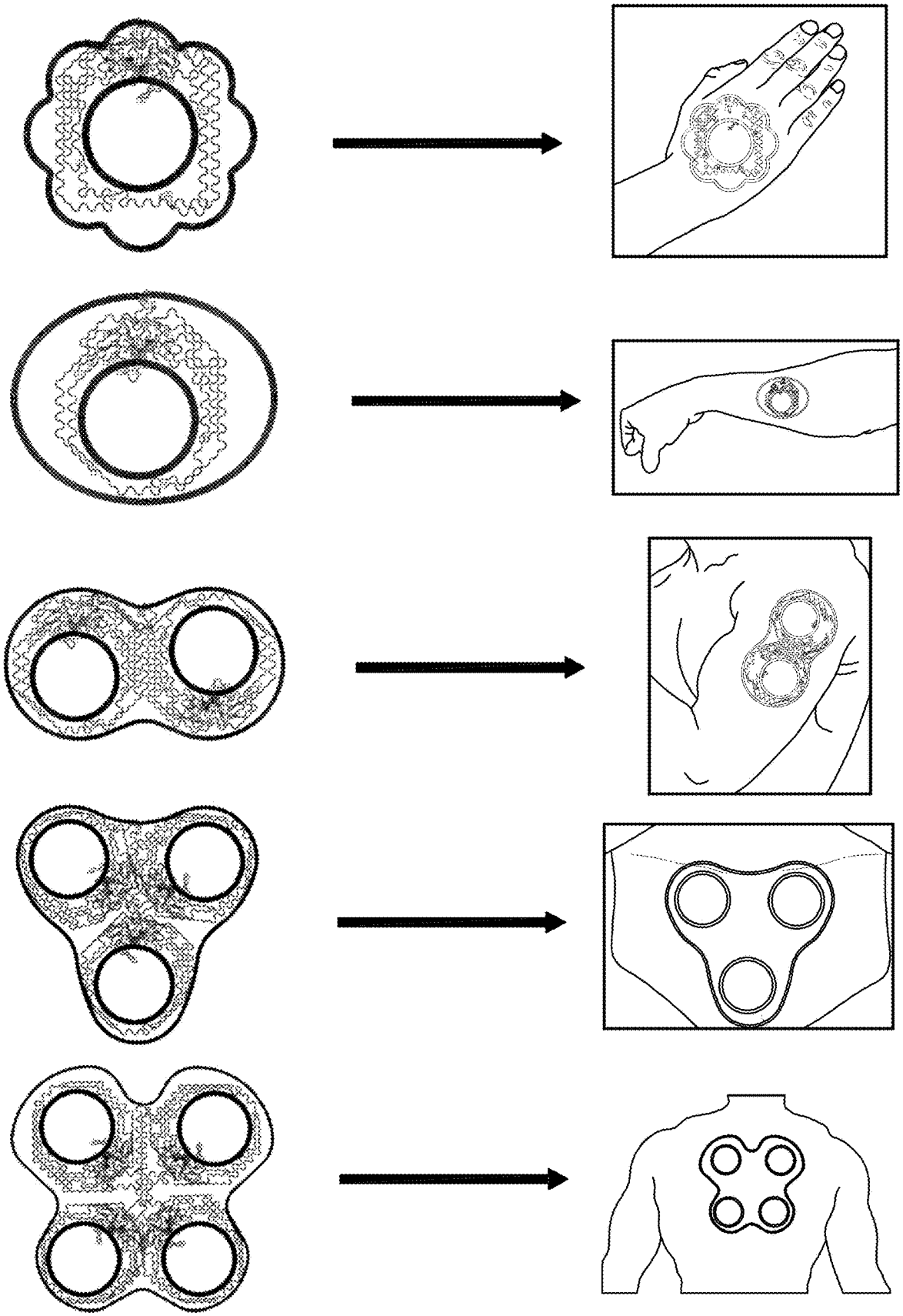
FIG. 24 provides examples of different epidermal VR devices for mounting to different locations on the body.

FIG. 24 illustrates the devices provided herein may be configured in any number of geometries tailored to where on the body the device is to positioned. For example, FIG. 24 illustrates the device mounted on the back of the hand, forearm, bicep, groin and back.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

For example, PCT/US18/15389 filed Jan. 26, 2018, titled "WIRELESS SURFACE MOUNTABLE SENSORS AND ACTUATORS" by Rogers et al. is specifically incorporated by reference, including for the sensors, actuators, wireless components (including power and communication systems, NFC chips, and the like).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a power range, an device number, actuator number, a frequency range, a length range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A virtual reality device comprising:
   a plurality of spatially distributed biologically interactive devices configured for interacting with a biological surface, each of the biologically interactive devices comprising: a sensor and an actuator;
   a wireless controller configured to receive operative command signals to control each of the biologically interactive devices and transmit to a remote controller output from each of the sensors; and
   a wireless power source operably connected to the plurality of biologically interactive devices,
   wherein the wireless controller operably controls the plurality of spatially distributed actuators by electrically energizing at least one individual actuator at a time with the other actuators in an off-state and cycling through all actuators at a switching frequency.

2. The virtual reality device of claim 1, wherein the plurality of spatially distributed biologically interactive devices are configured to generate a coordinated and spatiotemporally varying output of heat, electrical stimulation, mechanical vibration, or any combination thereof.

3. The virtual reality device of claim 2, configured for person-to-person interaction, further comprising a computer interface for control, at a distance by a person, of the plurality of spatially distributed biologically interactive devices.

4. The virtual reality device of claim 2, configured for gaming or training.

5. The virtual reality device of claim 1, wherein the sensors are configured to modulate the actuators based on one or more physiological parameters measured by the sensors.

6. The virtual reality device of claim 5, wherein said physiological parameters are: temperature; pressure; motion; location; blood flow; blood oxygenation; skin galvanic response; electrical impedance, modulus; sweat rate; biopotential; and/or strain.

7. The virtual reality device of claim 1, wherein the near field communication chip is configured to provide wireless power delivery to the sensors and the actuators and wireless data communication between the biologically interactive devices and an external controller.

8. The virtual reality device of claim 1, wherein the wireless controller provides two-way communication with the plurality of biologically interactive devices to acquire physiological parameter data from the sensors and to operate the actuators of the plurality of biologically interactive devices.

9. The virtual reality device of claim 8, wherein the wireless controller comprises a range reader.

10. The virtual reality device of claim 1, configured to provide sensing and actuating of an effective body surface area corresponding to at least 70% of a living animal skin surface.

11. The virtual reality device of claim 1, having a wireless transmission and receipt range that is greater than or equal to 10 cm.

12. The virtual reality device of claim 1, wherein the plurality of biologically interactive devices is directly or indirectly skin-mounted and provides a spatial distribution map of physiological parameters.

13. The virtual reality device of claim 1, wherein the plurality of biologically interactive devices are configured to directly connect to a skin surface of a living animal.

14. The virtual reality device of claim 1, wherein the plurality of biologically interactive devices are embedded or connected to a garment, wherein the garment is configured to be worn by a living animal to provide the plurality of biologically interactive devices adjacent to a skin surface.

15. The virtual reality device of claim 1, comprising at least 20 biologically interactive devices.

16. The virtual reality device of claim 1, wherein each biologically interactive device comprises:
a near field communication (NFC) chip for wireless communication and control;
a wireless energy harvester comprising a large area antenna for powering the actuators.

17. The virtual reality device of claim 1, wherein each of the sensors comprises:
a temperature sensor; and
a pressure sensor.

18. The virtual reality device of claim 17, wherein the pressure sensor comprises a silicon pressure sensor formed from a spiral shape layer of monocrystalline silicon.

19. The virtual reality device of claim 17, wherein the pressure sensor comprises a layer of silicon positioned between a top polymer layer and a bottom polymer layer.

20. The virtual reality device of claim 16, further comprising a magnetic inductive loop antenna configured to wirelessly interface with an external reader antenna.

21. The virtual reality device of claim 20, wherein the external reader antenna is embedded in an external reader antenna substrate.

22. The virtual reality device of claim 20, further comprising a remote controller that provides wireless commands to the wireless controller for remotely controlling the actuators.

23. The virtual reality device of claim 1, wherein each biologically interactive device is multifunctional and measures and/or controls at least temperature and pressure.

24. The virtual reality device of claim 1, wherein each biologically interactive device measures at least one additional parameter selected from the group consisting of: oxygen level, electric potential, heart rate, respiration rate, hypovolemia, and optical signal.

25. The virtual reality device of claim 1, wherein the wireless controller comprises a near field communication (NFC) chip having a plurality of outputs, with each output electronically connected to an individual actuator, and wherein the device further comprises a switch electronically positioned between the NFC chip output and the individual actuator to provide the individual actuator electrical energization at the switching frequency.

26. The virtual reality device of claim 25, wherein the switching frequency between the actuators is faster than a mechanoreceptor reaction time for a mechanoreceptor that is positioned beneath the actuation device during use, so that a simultaneous actuation of all the actuators is experienced by a user to whom the actuation device interfaces.

27. An actuation system comprising:
a plurality of actuation devices, each actuation device comprising:
a plurality of spatially distributed actuators, each actuator configured for interacting with a biological skin surface;
a wireless controller configured to receive operative command signals to control each of the actuators;
a wireless power system to power the actuators; and
a flexible substrate that supports each of the actuators, the wireless controller and the wireless power system; and
wherein each actuation device is in wireless communication with at least one other actuation device; and
wherein the wireless controller operably controls the plurality of spatially distributed actuators by electrically energizing at least one individual actuator at a time with the other actuators in an off-state and cycling through all actuators at a switching frequency.

28. The actuation system of claim 27, wherein
the wireless power system operably provides a power harvesting that is greater than or equal to 5 mW.

29. The actuation system of claim 27, wherein the wireless communication between the actuation devices is a two-way communication.

30. The actuation system of claim 29, wherein each of the actuation devices further comprises a sensor.

31. The actuation system of claim 30, wherein an output from at least one sensor is communicated to another actuation device to control the another actuation device actuators.

32. A method of virtual interaction with an individual, the method comprising the steps of:
providing a plurality of actuators spatially distributed over a skin surface of an individual;
wirelessly connecting the actuators to a remote controller;
inputting to the remote controller an input signal to activate at least a portion of the actuators and interface with the skin surface; and
wirelessly powering the activated actuators in a low power mode, wherein the low power mode comprises rapid switching between the activated actuators by electrically energizing at least one individual actuator at a time with the other actuators in an off-state and cycling through all actuators at a switching frequency.

33. A method of virtual interaction with an individual, the method comprising the steps of:
providing an actuator device including a plurality of spatially distributed actuators, system or virtual reality devices adjacent to a skin surface of an individual;
wirelessly connecting the actuators to a remote controller;
inputting to the remote controller an input signal to activate at least a portion of the actuators and to remotely interface with the skin surface;
thereby virtually interacting with an individual,
electrically energizing at least one individual actuator at a time with the other actuators in an off-state and cycling through all actuators at a switching frequency.

34. The method of claim 33, further comprising;
sensing one or more physical parameters with a sensor; and
transmitting an output from the sensor to the remote controller, thereby providing feedback to a remote user of the remote controller.

* * * * *